US00RE46731E

(19) United States
(12) Reissued Patent
Woycik et al.

(10) Patent Number: US RE46,731 E
(45) Date of Reissued Patent: Feb. 27, 2018

(54) COMPUTER-BASED ORDERING SYSTEM

(71) Applicant: Nextep Systems, Inc., Troy, MI (US)

(72) Inventors: Thomas Woycik, Birmingham, MI (US); Charles Wheeler, Waterford, MI (US)

(73) Assignee: Nextep Systems, Inc., Troy, MI (US)

(21) Appl. No.: 15/018,801

(22) Filed: Feb. 8, 2016

Related U.S. Patent Documents

Reissue of:
(64) Patent No.: 8,190,483
Issued: May 29, 2012
Appl. No.: 11/742,770
Filed: May 1, 2007

U.S. Applications:
(62) Division of application No. 14/289,923, filed on May 29, 2014, now Pat. No. Re. 45,882, which is an application for the reissue of Pat. No. 8,190,483.
(Continued)

(51) Int. Cl.
*G01C 21/00* (2006.01)
*B30B 11/20* (2006.01)
(Continued)

(52) U.S. Cl.
CPC ..... *B30B 11/201* (2013.01); *B30B 11/005* (2013.01); *G01N 3/565* (2013.01);
(Continued)

(58) Field of Classification Search
CPC ..... G06Q 50/12; G06F 3/00; G06F 3/033; G06F 3/0481
(Continued)

(56) References Cited

U.S. PATENT DOCUMENTS 5,353,219 A 10/1994 Mueller et al.
5,774,868 A 6/1998 Cragun et al.
(Continued)

OTHER PUBLICATIONS http://web.archive.org/web/20041013041513/www.new-realm.com/captiview.sub.- --ocd.htm, CaptiView Interactive Order Confirmation System, Archive of Website from Dec. 14, 2004.
(Continued)

*Primary Examiner* — Cameron Saadat
(74) *Attorney, Agent, or Firm* — Harness, Dickey & Pierce, P.L.C.

(57) ABSTRACT

A computer-based ordering system for ordering goods and services includes a plurality of self-service client terminals and a server. Each self-service client terminal runs a self-order application including a set of interactive menu screens having buttons that allow the customer to select and customize products for the order. An administration tool application communicates with the server to administer the self-service client terminals. The administration tool application including a menu editor that enables the administrator to create and edit the interactive menu screens provided by the self-order application at the self-service client terminals. The menu editor accesses a library of menu templates containing predefined groupings of buttons, and uses the menu templates, as directed by the administrator, during creation and editing of the interactive menu screens.

19 Claims, 28 Drawing Sheets

Related U.S. Application Data

(60) Provisional application No. 60/805,658, filed on Jun. 23, 2006, provisional application No. 60/746,226, filed on May 2, 2006.

(51) Int. Cl.

| | |
|---|---|
| ***G06Q 30/06*** | (2012.01) |
| ***G01N 3/56*** | (2006.01) |
| ***G07F 7/00*** | (2006.01) |
| ***G07F 11/00*** | (2006.01) |
| ***G07G 1/14*** | (2006.01) |
| ***B30B 11/00*** | (2006.01) |
| ***G06Q 20/36*** | (2012.01) |
| ***G07F 5/18*** | (2006.01) |

(52) U.S. Cl.
CPC ..... *G06Q 20/367* (2013.01); *G06Q 30/0601* (2013.01); *G06Q 30/0603* (2013.01); *G06Q 30/0621* (2013.01); *G06Q 30/0641* (2013.01); *G07F 5/18* (2013.01); *G07F 7/00* (2013.01); *G07F 11/002* (2013.01); *G07G 1/14* (2013.01)

(58) Field of Classification Search
USPC .... 705/15, 16; 715/700, 821, 823, 825, 826, 715/840
See application file for complete search history.

(56) References Cited

U.S. PATENT DOCUMENTS

| | | | |
|---|---|---|---|
| 5,774,871 | A | 6/1998 | Ferro |
| 5,897,623 | A | 4/1999 | Fein et al. |
| 6,014,137 | A | 1/2000 | Burns |
| 6,038,546 | A | 3/2000 | Ferro |
| 6,055,513 | A | 4/2000 | Katz et al. |
| 6,104,398 | A | 8/2000 | Cox, Jr. et al. |
| 6,119,099 | A | 9/2000 | Walker et al. |
| 6,223,163 | B1 | 4/2001 | Van Luchene |
| 6,317,835 | B1 | 11/2001 | Bilger et al. |
| 6,374,293 | B1 | 4/2002 | Dev et al. |
| 6,401,074 | B1 | 6/2002 | Sleeper |
| 6,529,879 | B1 | 3/2003 | Hasegawa |
| 6,598,024 | B1 | 7/2003 | Walker et al. |
| 6,634,550 | B1 | 10/2003 | Walker et al. |
| 6,636,835 | B2 | 10/2003 | Ragsdale-Elliott et al. |
| 6,694,300 | B1 | 2/2004 | Walker et al. |
| 6,810,385 | B1 | 10/2004 | Brady et al. |
| 6,940,393 | B2 | 9/2005 | Dev et al. |
| 8,190,483 | B2 | 5/2012 | Woycik et al. |
| 8,660,906 | B2 | 2/2014 | Woycik et al. |
| 2002/0010721 | A1 | 1/2002 | Crimmins et al. |
| 2002/0046124 | A1 | 4/2002 | Alderucci et al. |
| 2002/0052790 | A1 | 5/2002 | Tomishima |
| 2002/0077960 | A1 | 6/2002 | Kiely et al. |
| 2002/0147647 | A1 | 10/2002 | Ragsdale-Elliott et al. |
| 2002/0156682 | A1 | 10/2002 | DiPietro |
| 2002/0184104 | A1 | 12/2002 | Littman |
| 2002/0194074 | A1 | 12/2002 | Jacobs |
| 2003/0018531 | A1 | 1/2003 | Mahaffy et al. |
| 2003/0046166 | A1 | 3/2003 | Liebman |
| 2003/0163388 | A1 | 8/2003 | Beane |
| 2003/0236706 | A1 | 12/2003 | Weiss |
| 2004/0015401 | A1 | 1/2004 | Lee et al. |
| 2004/0024643 | A1 | 2/2004 | Pollock et al. |
| 2004/0035643 | A1 | 2/2004 | Dev et al. |
| 2004/0054587 | A1 | 3/2004 | Dev et al. |
| 2004/0143512 | A1 | 7/2004 | Sturr, Jr. |
| 2004/0158499 | A1 | 8/2004 | Dev et al. |
| 2004/0243471 | A1 | 12/2004 | Salmen et al. |
| 2004/0260607 | A1 | 12/2004 | Robbins et al. |
| 2005/0049921 | A1 | 3/2005 | Tengler et al. |
| 2005/0075934 | A1 | 4/2005 | Knight et al. |
| 2005/0107158 | A1* | 5/2005 | Kanisawa et al. ..... 463/30 |
| 2005/0160005 | A1 | 7/2005 | Roth et al. |
| 2005/0182681 | A1 | 8/2005 | Bruskotter et al. |
| 2005/0246223 | A1 | 11/2005 | Roth et al. |
| 2006/0006025 | A1 | 1/2006 | Dev et al. |
| 2006/0271442 | A1 | 11/2006 | Pfleging et al. |
| 2007/0005434 | A1 | 1/2007 | Roth et al. |
| 2007/0011058 | A1 | 1/2007 | Dev |
| 2007/0040026 | A1 | 2/2007 | Vleet et al. |
| 2007/0265935 | A1 | 11/2007 | Woycik et al. |
| 2008/0189172 | A1 | 8/2008 | Goren et al. |
| 2012/0133595 | A1 | 5/2012 | Lippolis et al. |
| 2012/0133596 | A1 | 5/2012 | Lippolis et al. |
| 2012/0136737 | A1 | 5/2012 | Lippolis |
| 2012/0179584 | A1 | 7/2012 | Woycik et al. |

OTHER PUBLICATIONS http://web.archive.org/web/20050307000112/www.hei-sei.com/product/f-pos.ht- m, FlexPOS Overview, Archive of Website from Apr. 1, 2005.

http://web.archive.org/web/20070211051411/www.interdynbmi.com/solutions/mi- crosoft-retail-mgmt.htm, Microsoft Retail Management Products, Archive of Website from Feb. 6, 2007.

DIY Promos Via Video POS; Touch Screens Offer Electronic Marketing, Apr. 1988, Chain Store Age Executive with Shopping Center Age. vol. 64, No. 4, Lebhar-Friedman Inc, p. 76.

Interactive POS Video Yield Instant Results; Vision Sustem Collects Data, Produces Coupons and Cash Refunds, Sep. 1988, Chain Store Age Executive wiht Shopping Center Age, vol. 64, No. 9, p. 52.

I-Mark Technology Enables Online Product Configuration and Direct Ordering for Spraying Systems Co.; Business Wire. New York: Nov. 24, 2003. p. 1; http://proquest.umi.com/pqdweb?did=462997701 & sid=2&Fmt=3&clientId=19649 &RQT=309&VName=PQD.

http://web.archive.org/web/20050405222709/http://www.comtrex.com/, Odyssey Software Suite; Archive of Website from Dec. 1, 2005.

http://web/archive.org/web/20050518080547/www.allurefm.com/product.sub.-o- rder.htm, Allure Order Confirmation Board Product Description, Archive of Website from Mar. 14, 2007.

http://web.archive.org/web/20050408131847/www..erconline.com/OCU.htm, AccuView Order Confirmation Display Product Overview, Archive of Website from Apr. 28, 2007.

Office Action for related U.S. Appl. No. 11/742,770, dated May 9, 2011.

Office Action for related U.S. Appl. No. 11/742,770, dated Jul. 21, 2011.

Notice of Allowance for related U.S. Appl. No. 11/742,770, dated Jan. 25, 2012.

Office Action for related U.S. Appl. No. 13/347,218, dated Sep. 13, 2012.

Office Action for related U.S. Appl. No. 13/347,218, dated Feb. 25, 2013.

Advisory Action for related U.S. Appl. No. 13/347,218, dated Oct. 9, 2013.

Notice of Allowance for related U.S. Appl. No. 13/347,218, dated Nov. 6, 2013.

Office Action for related U.S. Appl. No. 13/347,218, dated Aug. 5, 2013.

Amato-McCoy, Multi-Media Signage—Kicked Up a Notch!, Oct. 2002, Grocery Headquarters Magazine, vol. 68, Issue 10, p. 34.

Liddle, Vendor: Digital Deal Persuades Guests to Spend More, Nov. 27, 2000. Nation's Restaurant News, vol. 34, No. 48, pp. 50, 59.

McClure et al., What are the Hot Buttons in Produce Department POS?, Jan. 1992, Supermarket Business, vol. 47, No. 1, pp. 25, 70.

Zimmerman, Shop 'N Bag has POS in the Bag, May 15, 1995, Supermarket News, vol. 45, No. 20, p. 24.

Promotion System Marries Video and POS; SASI's Two Screen System is Less Sophisticated, but Less Expensive, Sep. 1988, Chain Store Age Executive with Shopping Center Age, vol. 64, No. 9, p. 56.

(56) References Cited

OTHER PUBLICATIONS http://web.archive.org/web/20050413221248/www.pager.net/htdocs/kiosk.html, Kiosk Product Overview, Archive of Website from Apr. 13, 2007.

* cited by examiner

COMPUTER-BASED ORDERING SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

[This application] *Notice: more than one reissue application has been filed for the reissue of U.S. Pat. No. 8,190,483; U.S. application No. 15/849,969 filed on Dec. 21, 2017 is a continuation reissue application of the present application; and the present application is a divisional reissue application of U.S. application Ser. No. 14/289,923, filed on May 29, 2014, now U.S. Pat. No. Re. 45,882, which is an application for reissue of U.S. Pat. No. 8,190,483, which* claims the benefit of U.S. Provisional Application No. 60/746,226 filed on May 2, 2006[. This application claims the benefit of] *and* U.S. Provisional Application No. 60/805,658 filed on Jun. 23, 2006.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates generally to computer-based systems used for ordering goods and services and, more particularly, to self-service terminals and software tools for administering self-service terminals.

2. Background Art

Point of Sale (POS) systems provide a means by which ordering and purchasing transactions can be carried out electronically at the store or other venue where the goods or services are supplied. Many of these POS systems are used by the merchants themselves to consummate transactions with their customers. Other POS systems comprise self-service terminals that can be used directly by the customer to order goods, pay for them, or both. The POS system generally includes at a minimum a processor-based terminal device along with software running on the processor to carry out the functions of the terminal. One or more remote computers are typically connected to the terminal by, for example, a computer network or dialup telephone connection to enable communication between the terminal and computer(s) for the purpose of carrying out the transaction (order, payment, etc.).

Self-service POS systems typically have a central computer acting as a server and one or more terminals which are the individual client units that are used by customers to input their orders. These terminals are often implemented as kiosks mounted to a floor via a base, or to a wall, or located on a counter or other raised surface. Each kiosk will include a computer display screen, possibly speakers for audio output, and one or more input devices such as a keyboard, key pad, or touch sensor overlaying the display screen. When a customer is interested in making a purchase, the kiosk allows customers to select products for purchase from those listed on the screen, submit an order for those products, and, in some cases, pay for the order.

Self-service POS systems typically use a dedicated server to communicate to each self-service client terminal. The server can be a general purpose computer located somewhere on the premises or remotely, and is programmed with software that is used to provide each client with product information for customer ordering. Changes to the products offered via the self-service terminals usually require access to and use of an administration program on the server using common input devices such as a keyboard and mouse to change the product offerings or information about those products (e.g., price).

Direct ordering of goods and services by customers can also be carried out using non-POS systems, such as Internet-based online ordering of goods from merchants for either pickup by the customer or delivery via shipment. These systems also commonly use a client-server topology to not only carry out the selection and ordering process, but also to complete payment for the goods.

SUMMARY OF INVENTION

It is an object of the invention to provide an improved computer-based ordering system for ordering goods and services.

The invention comprehends self-service terminals and software tools for administering self-service terminals.

In one approach to implementing a computer-based ordering system in accordance with the invention, a computer-based ordering system for ordering goods and services comprises a self-service terminal for use by a customer to place an order. The self-service terminal includes a processor and a storage medium storing a self-order application. The self-order application provides a first user interface including a set of interactive menu screens having buttons that allow the customer to select and customize products for the order. The storage medium further stores an administration tool application for administering the self-service terminal. The administration tool application provides a second user interface that can be accessed by the administrator to perform various administrative functions.

The administration tool application includes a menu editor. The menu editor enables the administrator to create and edit the interactive menu screens provided by the self-order application. The menu editor accesses a library of menu templates containing predefined groupings of buttons, and uses the menu templates, as directed by the administrator, during creation and editing of the interactive menu screens.

Preferably, the self-service terminal further comprises a display screen having a touch screen for accepting user input. Accordingly, the customer interacts with the self-order application using the touch screen. Further, the administrator interacts with the administration tool application using the touch screen.

In the approach described above, the self-service terminal includes a self-order application for use by customers and includes an administrative tool application for use by administrators. It is appreciated that other approaches to implementing a computer-based ordering system in accordance with the invention may involve a client/server environment.

In another approach to implementing a computer-based ordering system in accordance with the invention, a computer-based ordering system for ordering goods and services includes a plurality of self-service client terminals for use by customers to place orders, and a server in communication with the plurality of self-service client terminals. Each self-service client terminal runs a self-order application. An administration tool application is stored on a computer-readable storage medium. The administration tool application, when executed by a computer, communicates with the server to administer the self-service client terminals. The administration tool application includes a menu editor that enables the administrator to create and edit the interactive menu screens provided by the self-order application at the self-service client terminals. The menu editor accesses a library of menu templates containing predefined groupings of buttons, and uses the menu templates, as directed by the administrator, during creation and editing of the interactive menu screens.

It is appreciated that the administrative tool application could be located at a variety of places. For example, the administrative tool application may be located at the server. The server may also operate as an additional self-service client terminal by running the self-order application while the server communicates with the plurality of self-service client terminals in the background. Further, the administrative tool application may also be located at each client terminal to allow administration from any of the self-service client terminals. It is appreciated that there are many possible arrangements and the administrative tool application may be located at a variety of locations, including a back office location or an offsite location provided that the administrative tool application is able to communicate with the server.

At the more detailed level, the invention comprehends a number of additional features. Different implementations may employ different combinations of the comprehended features, depending on the application of the system.

In a preferred embodiment of the invention, the library of menu templates includes a plurality of templates. Each template represents an interactive menu screen having buttons. The menu editor enables the administrator to, during creation/editing of an interactive menu screen, select a template for the interactive menu screen and associate functions with the buttons included on the selected template.

The association of functions with the buttons included on a selected template may involve several additional features which are part of the preferred embodiment of the invention. For example, associating functions with the buttons included on the selected template may include selecting a button type for a button, selecting associated text for a button, selecting an image overlay for a button, and/or selecting an item/product for a button. Further in this aspect, associating functions with the buttons included on the selected template may include selecting a quantity for the item/product for a button, or selecting a pricing option for the item/product for a button. In another aspect, associating functions with the buttons included on the selected template may include selecting a subsequent menu screen for activation upon selection of a button by the customer. This creates a hierarchy of menus to guide the customer through the order process.

In addition to the various menu screen creating and editing, menu building, and administration tool related aspects of the invention described above, the invention also comprehends a variety of configurable button behaviors. For example, a template may be configured to allow selection of only a single button by the customer from a presented plurality of buttons. In another example, a template may be configured to allow selection of multiple buttons by a customer from a presented plurality of buttons.

The invention also comprehends special buttons. One example of a special button is a button including a plurality of sub-buttons to provide multiple selected states for the special button. Another example of a special button is a button that, upon selection thereof, causes selection of a predetermined set of a presented plurality of buttons.

In a computer-based ordering system, in certain situations, it is possible that orders from the self-service terminals could overwhelm the workers fulfilling the orders. The invention also comprehends an order governor for regulating the flow of orders, when needed.

In one approach to implementing a computer-based ordering system including an order governor in accordance with the invention, the system comprises a self-service terminal for use by customers to place orders. The self-service terminal runs a self-order application. The system further comprises an order display device for receiving orders placed by customers and providing instructions to workers that fulfill the orders. A configurable order governor cooperates with the self-order application to regulate the flow of orders. The flow of orders is regulated by introducing a wait time between customer orders at the self-service terminal, as needed, based on the order governor configuration.

It is appreciated that the order display device may take a variety of forms. For example, the order display device may be a video display screen that displays instructions corresponding to received orders. In the alternative, the order display device may be a printer that prints instructions corresponding to received orders.

In an exemplary implementation of the order governor, the order governor configuration includes a configurable value representing an average order fulfillment time. The wait time between customer orders is provided such that an order fulfillment backlog time stays below a predetermined value. More specifically, in this example, the order fulfillment backlog time is increased by the average order fulfillment time upon the placement of an order, and is decreased with the passing of time.

In another contemplated approach for implementing the order governor, the order governor configuration may include a plurality of configurable values representing order fulfillment time for the various products. In this approach, the order fulfillment backlog time is increased by an estimated order fulfillment time upon the placement of an order. This estimated order fulfillment time is based on the plurality of configurable values in the order governor configuration and the selected products for the placed order.

In yet a further contemplated feature of the invention, computer-based ordering systems may recognize customers through any one of many possible methods such as swiping a customer loyalty card, reading an RFID tag, swiping a credit card, or even through biometrics. Customer recognition allows the system to provide an enhanced customer experience, for example, by allowing returning customers to quickly order items ordered in the past without having to rebuild the order. A particular concern in customer recognition systems for computer-based ordering systems is that it is desirable, in certain circumstances, to recognize a customer without the need to store certain sensitive information. For example, it may be desirable to recognize a customer when the customer swipes a credit card; however, for some applications, it would be desirable to do this without storing sensitive customer information (for example, the credit card number).

The invention comprehends an approach to customer recognition for use in computer-based ordering systems wherein the customer is recognized based on encoded or encrypted information obtained from a one-way hash function (the term "hash function" as used herein is intended to encompass one-way hash functions as well as any equivalent algorithm that is very difficult to calculate in the reverse direction). For example, in an application where a customer credit card is swiped at the self-service terminal, the credit card number and/or other information fields obtained during the card swipe are encoded or encrypted using a hash function.

The encoded or encrypted result from the hash function is used to lookup the customer in a table or database, and the credit card number and/or other information fields obtained from the card swiping may be immediately destroyed, and not retained by the self-service terminal. The table or database where the customer is looked up may be stored, for example, at the local server for the ordering system. When the overall system includes a central server, for example, to coordinate multiple store locations, the table or database can be stored at the central server. Customer orders or other information that is to be retained to enhance the customer experience may be retained at the local server, and uploaded to the central server, for example, once per day. In the alternative, the ordering system could provide updates to the central server in real-time throughout the day.

DETAILED DESCRIPTION OF THE PREFERRED EMBODIMENTS

Figure 1:
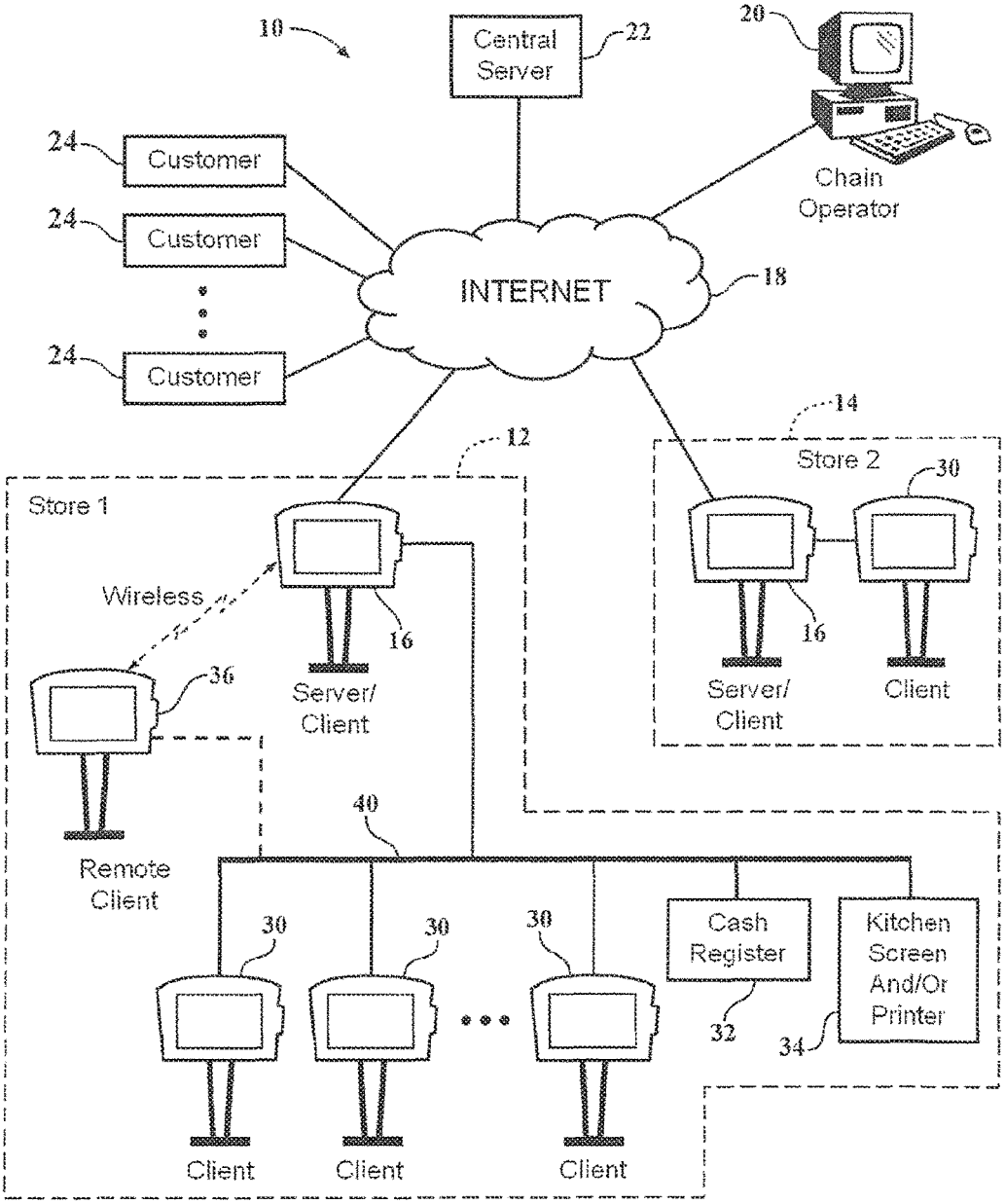
FIG. 1 illustrates an exemplary self-service ordering system made in accordance with the invention.

FIG. 1 shows an exemplary self service ordering system 10 constructed in accordance with the invention as it might be used by a chain of quick-service restaurants. The system 10 includes two store locations 12, 14 each having a plurality of kiosks arranged in a client-server configuration. In each store, the local (on-site) server 16 is connected to the Internet 18 which allows remote access by the restaurant chain operator 20 and enables the local server 16 to access a central server 22 for software and media updates. This Internet connection also makes possible use of the local server 16 for receiving online customer orders from customers 24. In general, a single store location will include at least one local server 16 and at least one client kiosk 30. In a more typical configuration such as is shown for Store 1 (store location 12), the store location will include a single server 16, multiple client kiosks 30, a cash register 32 (for cash, credit card, debit card, bar code card, or other payment means), and possibly a kitchen build screen or printer 34 for use by the food preparers in making and/or aggregating the food items for a particular order. The store location might also include one or more remote clients 36 (e.g., for ordering outside the store, but in a nearby location such as a drive-through kiosk, or at a kiosk located elsewhere in the same mall in which the store is located).

As indicated in FIG. 1, rather than using a dedicated "back room" computer as the local server, one of the kiosks 16 is used both as a client to permit customer entry of orders and as the local server to interface to the Internet 18 and to respond to requests from the local client kiosks 30. This is accomplished by providing separate client and server software both on a single one of the kiosks 16. The client software allows customer ordering of the food products available at the store. The server software interfaces with the client application on that same kiosk 16 as well as the other local kiosks 30 to provide them with the user interface (e.g., food ordering menus with their graphics and audio), and to receive orders from the client kiosks 30 and supply them to the kitchen screen/printer 34 as well as to the cash register 32 for payment by the customer.

As will be discussed in greater detail below, the client software is a computer program that is accessed by the user via a user interface application written using a multimedia authoring program. For customer ordering of food items, the user interface application is a self-order application that displays a graphic-intensive user interface that allows the customer to select and customize the desired food items, specify quantity, options, etc. Additionally, the local server kiosk 16 further includes an administrative tool comprising a second user interface application that can be accessed by the administrator to perform various administrative functions such as configuring kiosks, creating and editing menus and available food items, and specifying tax and payment features of the system. This administrative tool is also written using a multimedia authoring program that provides an administrative user interface to the client program. During normal use, the server process runs in the background while the food ordering client software application provides the same user interface (screen display, touch screen input) as the other client kiosks 30. When access to server administration is needed, the store owner or other administrator can switch to the administrative tool on the server kiosk 16. As will also be discussed further below, the system also allows the administrative tool to be run from any of the local clients 30, and this can be done, for example, by loading the administrative tool on each client computer 30.

The local kiosks 30, cash register 32, and kitchen screen/printer 34 are connected together via a local area network 40 that uses TCP/IP over an Ethernet connection. The remote kiosk 36 can also be hardwired to this LAN 40 or can be connected to the local server 16 or a node on the LAN 40 via a wireless connection. Similarly, any or all of the local client kiosks 30 or other devices at the store location 12 can be connected to the network 40 via a wireless link. The network 40 can be any IP-based network, including LANs, WANs, VPNs, and it will be appreciated that network addressing schemes other than IP can be used. Although not shown, the cash register 32 or another device on the network 40 can be connected to a credit card payment center either via the Internet 18, a telephone connection, or a wireless communication network (e.g., cellular data network) to process customer payments. As indicated in FIG. 1, Store 2 (store location 14) can have a simple one or two kiosk setup without any of the additional components shown in connection with Store 1 (store location 12); however, the more typical configuration will include a merchant order processing device such as a cash register 32 and/or display screen/printer 34 for use by the merchant to carry out and complete the transaction.

Although customer orders are typically received via one of the local kiosks 30, the central server 22 can be used to provide a web interface between the customers 24 and local server 16. This enables customers 24 to place orders remotely using a standard web browser. Various suitable ways of implementing online ordering and integration of that into a local ordering system are known to those skilled in the art. Remote access also allows the chain operator 20 to remotely run the administrative tool. This can be done several ways. One is for the chain operator 20 to have the administrative tool loaded on a remote computer. For this, the remote computer can access the configuration information (menu screens, items, and other settings) at the local server 16, then allow the operator to make changes, and then update the local server 16 with the new configuration information. A second approach is to have the administrative tool loaded on the central server 22 and then provide the chain operator 20 with web access to the central server 22. In this approach, the central server 22 then accesses and stores updated configuration information on the local server 16. A third approach is to provide a web interface to the administrative tool on the local server 16 so that the chain operator 20 can access this interface from any Internet connected general purpose computer using the IP address of the local server 16. This can be done using any of a number of different remote access and control approaches known to those skilled in the art. Other means of providing remote administration of the kiosks can be utilized.

As noted above, the central server 22 can be used to provide software and media updates to the local servers 16. Furthermore, the central server 22 can provide additional optional features to the system 10, such as remote diagnostics of kiosks, automated kiosk installations, data repository, centralized reporting, etc. Where no central server 22 is used on the system, remote ordering by customers 24 over the Internet can still be provided by using the local server 16 as a web server configured to allow online ordering.

Figure 2:
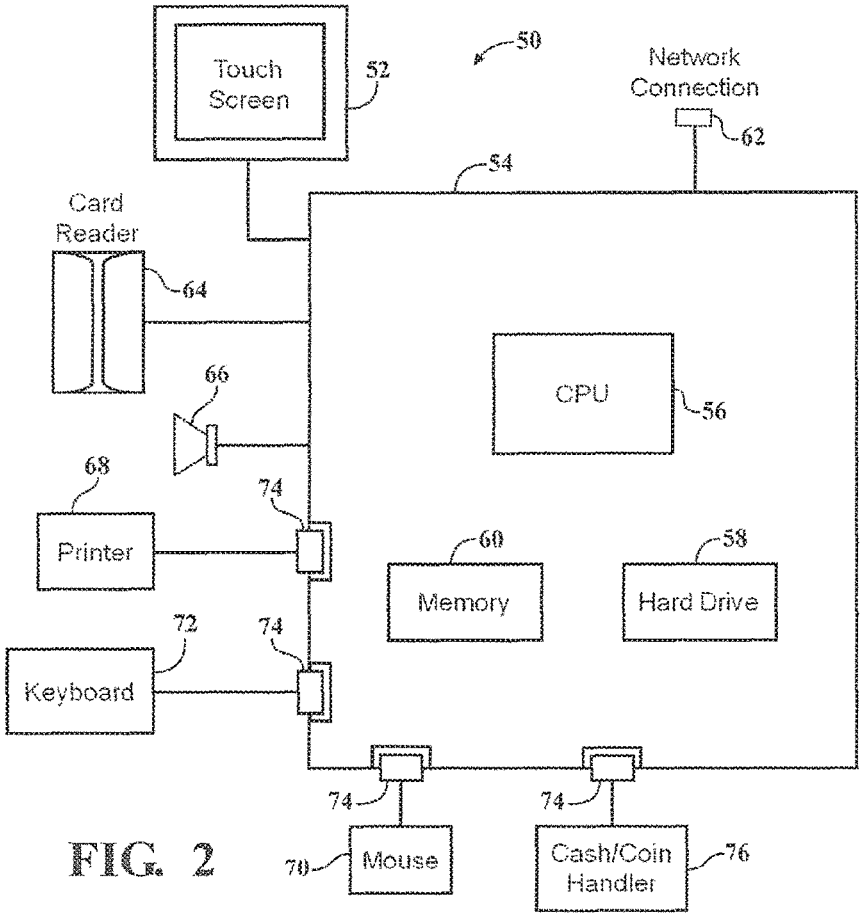
FIG. 2 illustrates an exemplary kiosk of the ordering system.

Turning now to FIG. 2, there is shown one embodiment of a kiosk of the ordering system. The kiosk 50 includes most of the elements commonly found in a general purpose computer, including a display screen 52 and motherboard 54 having a central processing unit (microprocessor) 56, hard drive 58, solid state memory 60, and a network connection 62. Connected to the motherboard 54 are the display screen 52, a card reader 64 (e.g., magnetic or bar code) for data input, and a speaker 66 for audio output. Other devices such as a printer 68 can be attached or integrated into the kiosk 50. The display screen 52 is implemented as a touch screen that operates as both a display unit and an input device for use by customers and administrators. Other displays and input devices can also be used, such as a standard CRT, LCD, mouse 70, keyboard 72, etc. For this purpose, the motherboard 54 includes additional ports 74 (e.g., USB) for connecting a printer 68, keyboard 72, and mouse 70. While these additional input and output devices can be included as a permanent part of the kiosk 50, the system is designed so that both customer use and administration can be carried out via the touch screen 52 only. Also, as indicated in FIG. 2, a cash handler 76 can be directly connected to the kiosk 50 to carry out validation of the bill and receipt and dispensing of cash. The solid state memory 60 may include RAM, ROM, and/or any other suitable computer-readable memory. The network connection 62 may be implemented using a wireless device for communication through WI-FI, Bluetooth, or other suitable wireless communication protocols, or may include a hardwired connection to a LAN or WAN.

Figure 3:
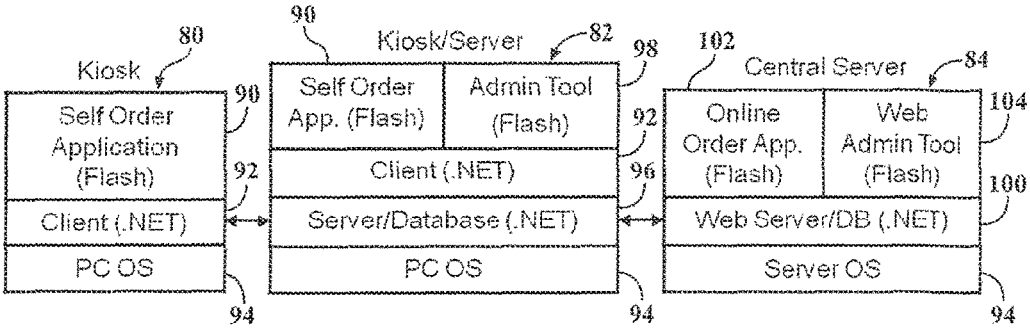
FIG. 3 illustrates the various software layers running on the client kiosks, client/server kiosk, and central server in the exemplary self-service ordering system.

FIG. 3 illustrates the various software layers running on the client kiosks 80, client/server kiosk 82, and central server 84. As mentioned above, in use the client program is accessed via a user interface that is provided using the touch screen to enable customers to use the system. This is carried out using a multimedia authoring tool to develop a graphical user interface application 90 that runs atop a web services layer 92 that provides the underlying client functionality. At the bottom software layer is the base operating system 94, such as Microsoft Windows™ XP or WePOS. This operating system includes the .NET Framework. VS.NET, ASP.NET and/or Windows Forms are used for programming to provide the basic client functionality. The user interface to this .NET application is preferably Macromedia Flash™ content (e.g., .swf files) or some other enhanced vector graphics file format such as SVG. The use of Flash content developed through, for example, ActionScript and as a graphical user interface to Microsoft.NET programming is known to those skilled in the art. Thus, in the illustrated embodiment, the software stored on each kiosk 80 includes a combination of a client computer program 92 (e.g., written in .NET) and user interface content 90 stored in an enhanced vector graphics file format, with this content being used by a suitable player or virtual machine (e.g., Macromedia Flash Player) to generate the user interface on the touch screen.

For the server kiosk 82, it includes not only the client program 92, but also a server program 96 (including its associated database) as well as an administrative tool 98 for configuring the server program 96. The administrative tool 98 is also implemented through the use of an enhanced vector graphics user interface overlying the Microsoft.NET client program 92 which handles communication between the administrative tool 98 and server program 96. As used herein "enhanced vector graphics" and "enhanced vector graphics file format" refer to files that support either multiple vector graphics (such as are used in displaying animations) and/or single vector graphics in conjunction with other content that can be displayed (e.g., text, video, raster-based graphics) or otherwise supplied (e.g., audio) to the user. Again, SWF and SVG files are two examples of this format. Another suitable format is the XAML format used by Microsoft Windows Presentation Foundation™. XAML presentations can be generated using the Microsoft Expression Interactive Designer™ tool. However implemented, the administrative tool 98 can include the same functions typically used to add, delete, and configure kiosks in the system, to make global settings (e.g., set time, sales tax percentage, receipt header and footer text), to create display screens (e.g., food ordering menus), to create a list of food items that are used on the different menu screens, and to edit the various attributes of the food items (e.g., name, associated graphic, price). For other (non-food service applications), the administrative tool 98 would provide somewhat different functionality and control. Accordingly, the various features and organization of the administrative tool 98 can be determined as desired for a particular application.

In the illustrated embodiment, the administrative tool 98 is not only produced using the combination of enhanced vector graphics content overlying a programming software layer (such as .NET), but the software architecture is used in conjunction with the touch screen of the kiosk to enable complete administration of the system via the local server kiosk, and, if desired, this can be done without the need for additional input devices such as a keyboard or mouse. Thus, the store owner or chain operator can carry out administration of the system using a simplified user interface that requires little if any training or experience with computers. Furthermore, the web services platform provided by .NET can be used to provide remote administration by the chain operator from any Internet-connected computer (such as a home office computer) so that various store locations can be configured from a single computer. The programming needed to implement this software architecture strategy is known to those skilled in the art.

The central server 84 can likewise be implemented using Flash movies or some other enhanced vector graphics files that interface directly to a web server program 100. The central server 84 can include both a web based online order application 102 as well as a web based administration tool 104. Again, the programming used to implement this approach will be known to those skilled in the art.

Figure 4:
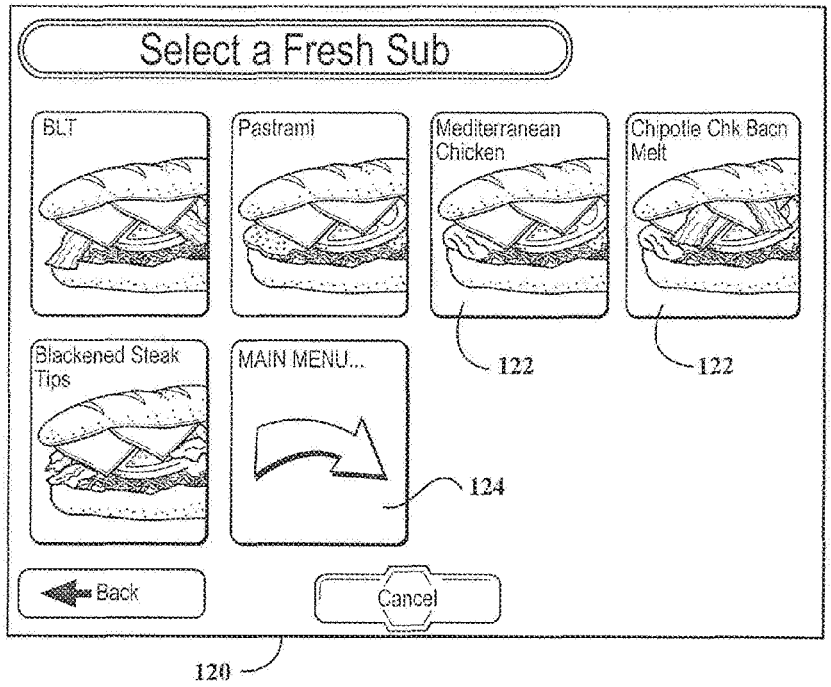
FIG. 4 depicts a sandwich selection screen provided by the self-order application running on a kiosk in the exemplary self-ordering system.
Figure 5:
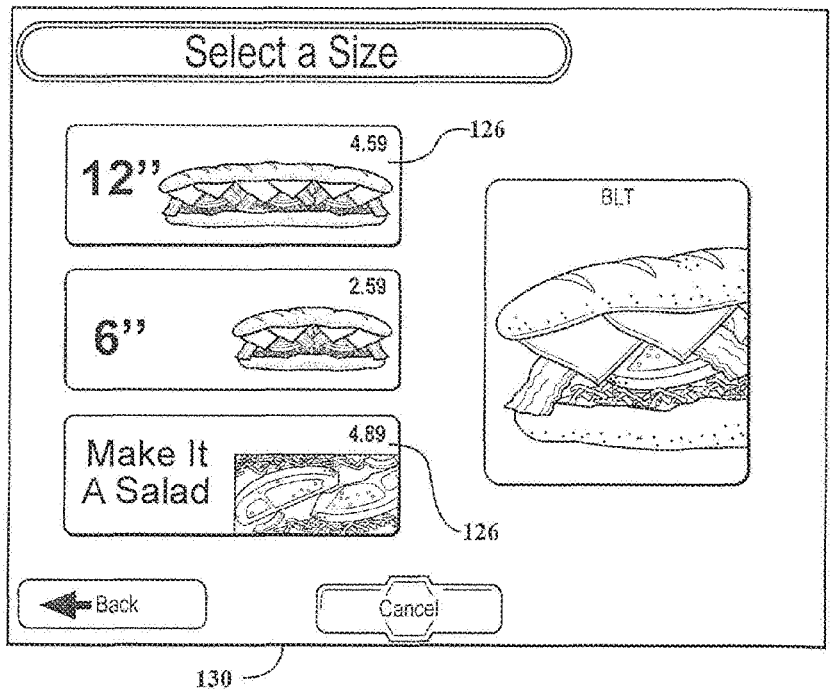
FIG. 5 depicts a succeeding screen in which a first set of options for a selected sandwich are provided.
Figure 6:
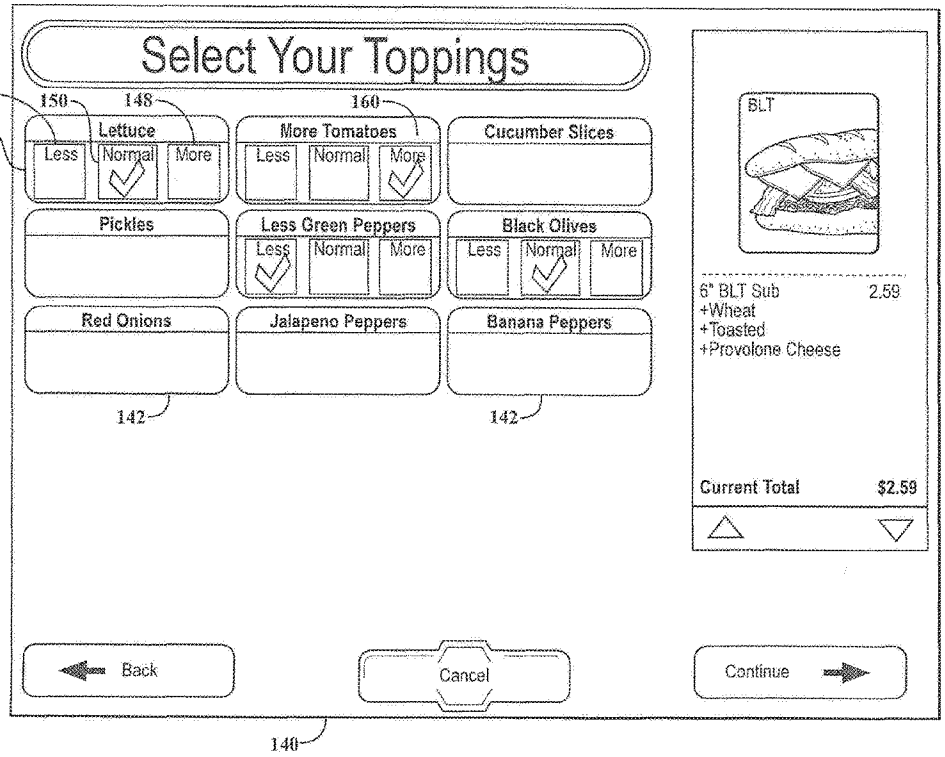
FIG. 6 depicts a subsequent screen in which additional options for the sandwich are provided, including the use of less/normal/more overlay buttons.

Various features and uses of the self-order application (customer user interface) 90 and the administrative tool 98 used on the kiosks will now be described. The self-order application 90 provides a set of interactive screens that guide the customer through the process of placing an order. The interactive screens contain menus of available items and/or options displayed on the touch screen through the user interface software. For example, FIG. 4 depicts a sandwich selection screen 120 which allows the customer to select (buttons 122) an item (particular type of sandwich) or return (button 124) to the main item ordering menu (not shown) where the different categories of food available are provided (e.g., sandwiches, salads, drinks, side orders, etc.). FIG. 5 depicts a succeeding screen 130 in which a first set of options (buttons 126) for the selected item (BLT sandwich) are provided. On this screen, the customer is able to select the size of the sandwich, or is able to change the sandwich order into a similar type of salad. FIG. 6 shows a subsequent screen 140 in which additional options (buttons 142) for the sandwich are made available, in particular, the different types of toppings that can be added to the sandwich. Note that, at the right side of these option screens, the item and previous options selected are shown along with the corresponding prices. For the purpose of making these selections on the various screens, each menu contains a series of buttons displaying the selectable items/options. The buttons contain graphics and/or text to identify the selections available to the user. The buttons may also be animated through the use of the Flash content to provide added visual effect to the customer.

Multiple button types are used to guide the customer through different scenarios that may be encountered during the ordering process. These button types include menu buttons (MenuButton), select one buttons (SelectOne), single modifier buttons (SingleMod), multiple modifier buttons (MultipleMod), select other buttons (SelectOther), quantity buttons (Quantity), less/normal/more buttons (LNM), and none/normal/extra buttons (NNE), each of which are described below. MenuButtons allow the customer to select a category to reach submenus in the system. For example, MenuButtons are used by the customer to select a category of food, such as sandwiches or side order items or drinks. As another example, a menu may ask the customer if they would like to select an additional item when ordering a meal and, for that purpose, the menu includes a MenuButton to allow the customer to decline the offer. Upon selection of a MenuButton, the software navigates to a new screen or submenu to continue the ordering process. SelectOne buttons allow customers to select a single item from a menu, such as a particular sandwich from a sandwich menu, and immediately jump to another menu based on the selection. Thus, SelectOne buttons differ from MenuButtons primarily in that the SelectOne buttons are used by the client software to register the selection of an item or option prior to moving to another display screen, whereas the MenuButtons are used primarily just to navigate to another screen without any selection of an item or option.

SingleMod buttons allow customers to select a single modification option (e.g., an ingredient or topping) for an item from a menu and immediately jump to another menu based on the selection. A button for adding cheese to a sandwich may be an example of a SingleMod button. Another example of a SingleMod button is selecting one salad dressing from a list of many salad dressings. MultipleMod buttons, examples of which are shown in FIG. 6 (buttons 142), allow customers to select multiple options (e.g., ingredients or toppings) for an item from a single menu before continuing on in the ordering process. SelectOther buttons group multiple items together on a menu so that touching the SelectOther button will select multiple items on the menu. For example, activating a SelectOther button titled "the works" on a menu displaying ingredients could select all the ingredients listed on the menu. Quantity buttons allow customers to select the quantity of an item to add to an order. Pressing a Quantity button launches a pop-up type menu containing a number pad to allow the customer to enter the quantity.

Figure 7:
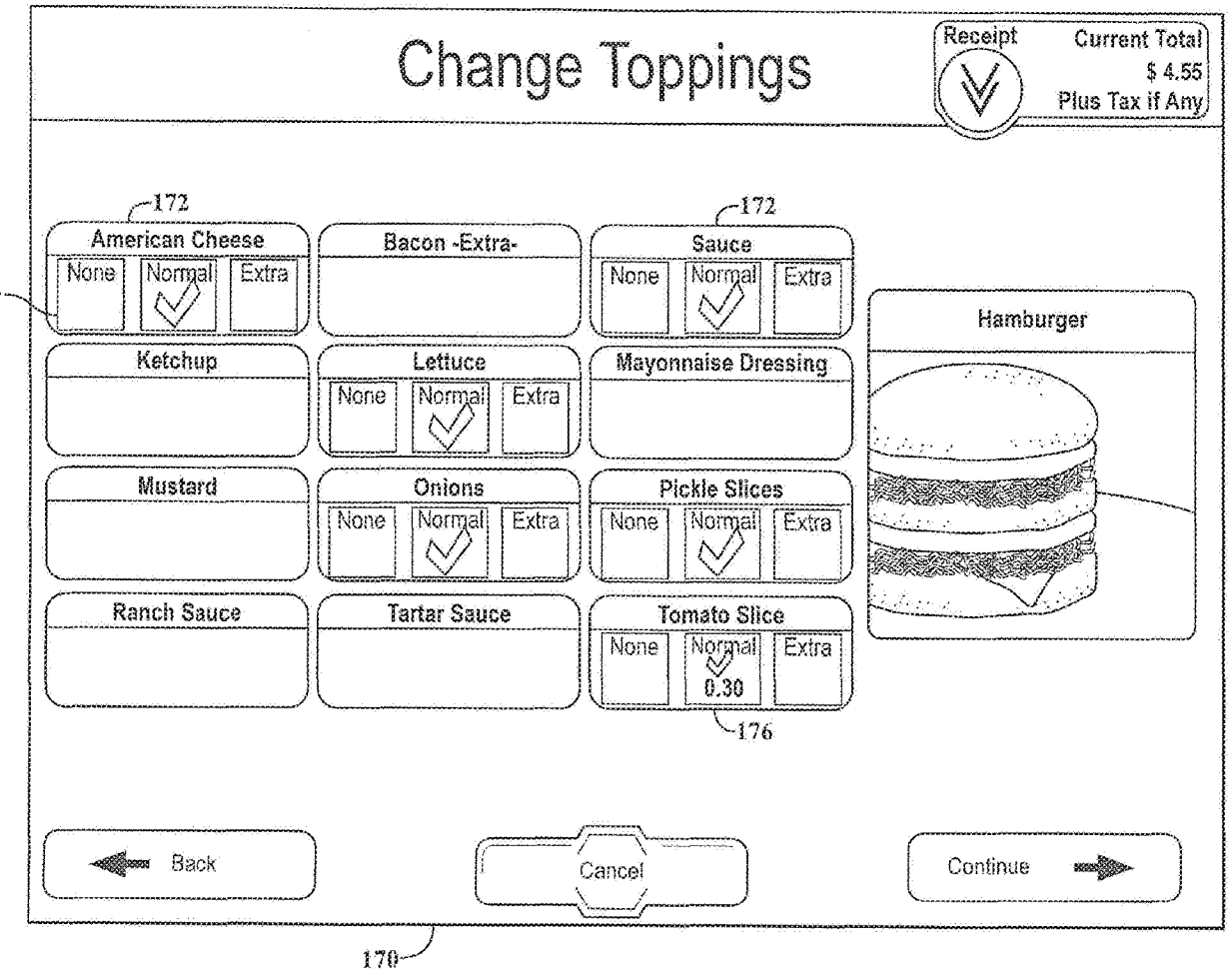
FIG. 7 depicts a subsequent screen in which additional options, in this case for a hamburger, are provided, including the use of none/normal/extra overlay buttons.
Figure 8:
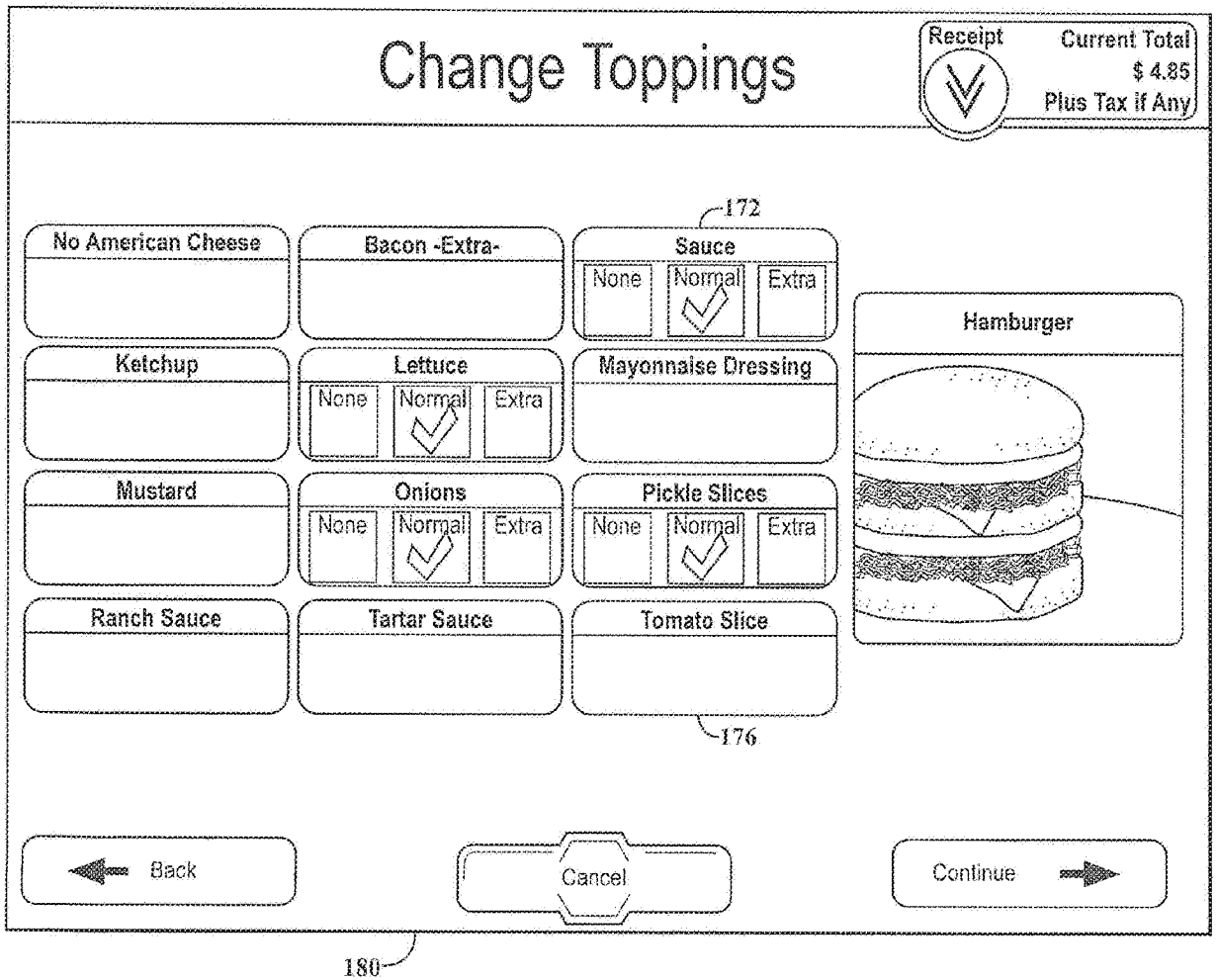
FIG. 8 depicts a subsequent screen to the screen shown in FIG. 7, where the American Cheese overlay buttons have been eliminated and new overlay buttons are displayed on the tomato button.
Figure 9:
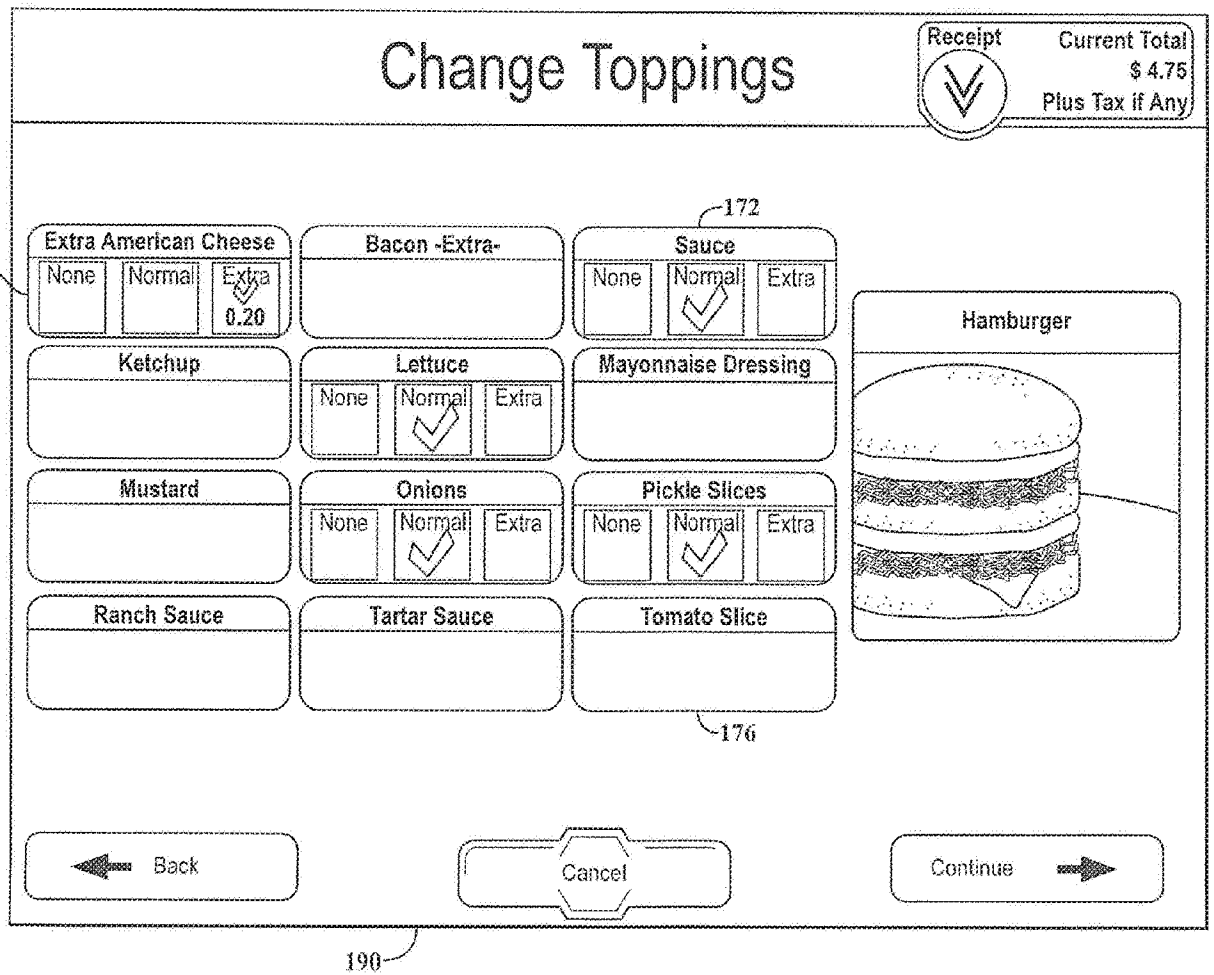
FIG. 9 depicts another subsequent screen to the screen shown in FIG. 7, where additional cheese has been selected.

The self-order application also includes two multi-part buttons types: less/normal/more (LNM) buttons shown in FIG. 6, and none/normal/extra (NNE) buttons, shown in FIGS. 7-9. Less/normal/more buttons allow the customer to modify the amount of a particular ingredient to use in preparing a food or beverage item selected by the customer. For example, when ordering a sandwich, a condiments menu may contain buttons to select sauces to add to the sandwich and how much of each sauce to use. Another such example is shown in FIG. 6 in which a menu of available toppings is shown. For this menu, the initial (default) setting of the program is that none of the toppings are selected. If the customer wishes to specify a particular topping, the customer presses on the touch screen at that topping's button at which point the button graphic changes to identify three smaller sized overlay buttons labeled "less," "normal," and "more," with a check mark appearing on the "normal" overlay button by default. See, for example, the "Lettuce" button 144 in FIG. 6. The user can then change the amount of the topping to be added to the sandwich by pressing either the "less" or "more" overlay buttons 146 and 148, respectively, in which case the "normal" overlay button 150 is unchecked and a check mark is placed on the selected overlay button. Each such selection is registered by the client program and used to build the food order. To remove a selected topping that has been chosen, the customer can simply press on the checked overlay button, and this action is recognized by the software as a request to deselect the topping entirely, in which case the graphic is changed back to the default in which the overlay buttons are eliminated from the display. Note that where more or less of a topping is selected, the identifier for that topping (e.g., "Tomatoes") can be changed (e.g., to "More Tomatoes") to reflect the altered (less or more) amount (button 160).

Thus, it can be seen from FIG. 6 that the system can provide a single menu screen that includes a number of independently selectable buttons, some or all of which can be activated to display additional buttons (e.g., overlay buttons) that permit not only selection of the particular item or option identified by the button, but to customize or modify that selection (e.g., less/normal/more). The additional buttons can be separate buttons or sub-buttons located adjacent the button they modify, or can be overlay sub-buttons that are either fully opaque or, as shown, are superimposed on the button in a semi-transparent manner. By using the overlay buttons, the system allows a high level of customization of the food order by the user in a manner that (1) does not take up additional screen space or display screens and (2) is highly intuitive in use while requiring minimal input from the user.

This sub-button use need not be limited to modification of quantity, but instead can be used for other purposes that will become apparent to those skilled in the art. In this regard, although the disclosed sub-buttons are programmed as mutually-exclusive selections (i.e., selecting one sub-button deselects the currently selected sub-button for a particular button), they need not be, depending on the options associated with the sub-buttons, and instead the system could allow plural sub-buttons to be selected at the same time.

Referring now to FIGS. 7-9, a further example of the use of the overlay type of sub-buttons is shown. In this example, rather than using less/normal/more, the overlay button options are none/normal/extra. The none/normal/extra overlay buttons are useful for food items that have a standard list of ingredients, such as in the specialty sandwich shown in the screen 170 depicted in FIG. 7. Thus, when the customer initially selects the restaurant's standard hamburger, the options menu of FIG. 7 is displayed which not only includes all of the available toppings (as in FIG. 6), but which has as its default those ingredients checked "normal" that come standard on the hamburger. The customer can then make changes as desired, adding other toppings, or changing the selection of default toppings to increase the amount of the topping (the extra sub-button), or to eliminate the topping altogether (the none sub-button). Thus, for example, in FIG. 7 there is shown a toppings menu for a hamburger which by the restaurant's default has American cheese, lettuce, onions, pickle slices, and a sauce as standard ingredients. FIG. 7 shows each of those ingredients on the menu represented with the none/normal/extra overlay buttons 172. If the customer desires to eliminate the cheese and add tomatoes, they select "none" (overlay button 174) on the American cheese button and select the tomato slice button 176, in which case the changes are registered by the system, the American Cheese overlay buttons are eliminated, and new overlay buttons are displayed on the tomato button, as shown in the screen 180 depicted in FIG. 8. Also, to help highlight this change, the identifying text on the cheese button is changed from "American Cheese" to "No American Cheese." The button may also provide pricing information related to the cost of selecting a non-standard option, such as the tomato slice, in which case this incremental cost is overlayed on the tomato slice sub-button along with the check mark. Similarly, eliminating or increasing the amount of a standard item might alter the sandwich price. Thus, as shown in the screen 190 depicted in FIG. 9, where additional cheese is desired and has been selected by the customer, a check mark is placed under "extra" for the American cheese and the additional cost is overlayed on the sub-button along with the check mark (button 192).

Customers generally begin an order at a kiosk by tapping on the touch screen of the kiosk. The kiosk displays a top menu of categories determined by the administrator. The customer may then begin selecting items, modifying ingredients, adding side items, etc. Alternatively, the order may begin using customer recognition by the system. The system may recognize customers locally through any one of many possible methods such as swiping a customer loyalty card, reading an RFID tag, swiping a credit card, or even through biometrics such as thumb, retinal, and/or facial recognition. Once a customer is recognized, the system displays a message welcoming the customer and displays a list of previous orders by the customer. The previous orders list allows the customer to begin the current order with a customized item or set of items from a previous order, rather than having to go through the process of recreating the same item or complete order from scratch. The customer may choose to duplicate an entire previous order or individual items from that order. Selecting a previous order brings up a list of specific items within the order, and the customer may select the entire previous order or can simply select an item to customize (if desired) and add to his current order. If the customer is satisfied with the item he may select to continue with his current order. If the customer wishes to modify the contents of the item selected, he may do so by touching one of the contents on the touch screen. Thus, using customer recognition, returning customers can quickly order items ordered in the past without having to rebuild the order each time they use a kiosk. For this purpose, the system tracks customer orders and stores them on the server. Where the central server 22 of FIG. 1 is used, the customer orders can be stored at the central server 22 to provide a centralized storage approach that then permits the prior orders to be accessed from the central server 22 regardless of the particular store at which the customer is located. By the use of customer recognition, the system is able to determine the frequency of customer visits and track customer habits and tastes. Using this information, the system can then recommend new or additional products to the customer, or can provide the customer with a customer loyalty discount or award.

Other features assist customers in placing orders. For instance, pricing information is updated live on the display as the customer selects or deselects items. Pricing is updated as items are added to or removed from the order, as well as for ingredients that have extra charges or credits associated with them. In the example noted above in FIG. 8, adding tomato slices to the sandwich described incurs an extra charge that is added to the pricing information when the tomato slices are selected. In another feature, animation "nudges" are use to urge the customer along in the ordering process if it appears that the customer is stuck on a particular screen. For example, if a customer is inactive for 5 seconds, the self-order application may highlight the most likely next step such as highlighting a particular button that is most likely to be the next button activated.

The self-order application also includes an upsell feature to suggest other items or increase portions based upon the items already selected or the order history of recognized customers. The upsell feature shows the customer a cost savings for combining the extra item with those already selected. For example, if the customer orders a sandwich and a drink, the system may ask if the customer would like to include a side item such as chips or French fries with them for a specified amount. The system also shows the customer that ordering the new combination would save the customer money compared to ordering the items individually. The system may also ask if the customer would like to increase the serving sizes of the drink and sides, or may even ask if the customer would like to add other additional items such as a dessert.

The self-order application can also accept payment at the kiosk or prompt the customer to pay at a specific location. Optional magnetic strip card readers allow users to pay by credit card, debit card, or accounts associated with customer loyalty cards or IDs. Other types of fully or partially automated payment approaches can be used such as RFID systems—the Paypass™ system available front Mastercard of Purchase, NY (www.mastercard.com) being one such example. The system may include an optional printing device to print out a receipt for the order and include information regarding the order such as price, payment information, a listing of items purchased, and even nutritional information. The nutritional information is calculated by the system based upon the items purchased, their ingredients selected, and the quantities requested. The system may also display the nutritional information of the items live on the screen as ingredients added or removed or their quantities varied for an item.

As noted above, customers are not limited to placing orders at kiosks. The system also includes remote web service to allow customers to place orders using a standard web browser via the Internet. The remote ordering can be handled either using the central server or the local server kiosk which includes a web server. The central server is useful for chain restaurants and can be used to either direct the customer to a particular store and its local web server, such as by a URL link on the central server website, or can accept and process the order itself, with the order then being transmitted to the particular store selected by the customer during the online ordering process. Where the food is to be delivered rather than picked up by the customer (e.g., in pizza delivery), the central server need not have the customer specify a store location, but rather just their address (or a landline phone number that is used to obtain the address), or using customer recognition from past orders can lookup this information in the server's database, and this information can then be used by the server to determine which store will handle the order and delivery. The specifics of the particular store's menu and availability of food items can be taken into account in the order process, and this information (such as the store being out of banana peppers) can be stored either at the local store's server and accessed by the central server during ordering, or such information can be stored at the central server itself with the local server periodically updating such information on the central server. By whatever approach is used for online ordering, the web server provides a web based interface similar to the self-order application interface on the kiosks. To help minimize the bandwidth needed for implementing the online ordering, the system uses vector graphics for most pictures and graphical symbols. These vector graphics can also be used on the local (in-store) networks when media is being transferred between the server kiosk and client kiosks. The online ordering process is generally the same as the process used at a kiosk with a few exceptions. For example, customer recognition may include the use of cookies or a login ID.

Additional customer information such as customer addresses, credit card information, payment preferences, etc. may be stored on the server for use in kiosk ordering, online ordering, or both.

Once an order is placed, regardless if at a kiosk or through a web client, the system generates a kitchen build for each item in the order. A kitchen build is a set of instructions for making each particular item, including the ingredients needed, the amount of each ingredient, and the order of assembly for the item. The information on the kitchen build may vary from the information printed on the customer receipt in both detail and sequence. The information on the kitchen build may also be in a different language than the information printed on the customer receipt. The kitchen build is sent to a kitchen printer and/or kitchen video system (KVS) where the order is prepared according to the build instructions.

Administration

The local server kiosk (16, FIG. 1; 82, FIG. 3) includes an administrative tool (98, FIG. 3) to run reposts, check the system status, add or remove kiosks from the system, or edit the screen displays that the customers see. All of these settings are stored on the local server 16, 82. The administrative tool 98 allows an administrator to modify these settings via a local kiosk touch screen. The administrative tool 98 is built using the same enhanced vector graphics approach (e.g., FLASH and .NET) described above for the self-order application interface so that administrators can setup menus and items, and change configuration items primarily via a kiosk touch screen. Therefore, the administrative tool 98 provides a graphical representation of menu options, button selections, images, text fields, etc. on the kiosk. Those items are readily editable through the graphical administrative tool 98 as will be discussed in more detail below. An advantage of this approach is that it enables administrators and store owners to make changes to the store offerings and customer interface without requiring any knowledge of the underlying code. In addition, administration is available from any client kiosk (30, FIG. 1; 80, FIG. 3) configured to communicate with the server 16, 82. This can be implemented by, for example, storing the administrative tool 98 on each client kiosk 30, 80 or by providing the system with the ability to execute the administrative tool 98 on the server 16, 82 using an application interface located on the client kiosks 30, 80. Where the administrative tool 98 is separately stored on each client kiosk 30, 80 and run locally on the client, the tool can be configured with the server IP address of the server kiosk 16, 82 so that, prior to giving the administrator access to change the kiosk, menu, and item setups, it verifies that there are no other instances of the administrative tool 98 running. Also, in this implementation, the configuration data for the kiosks, menus, and items can be stored on the server kiosk 16, 82 and downloaded to the client kiosk 30, 80 when the administrative tool 98 is run at the client. Changes to the configuration are then uploaded back to the server kiosk 16, 82 when the administrator is done. Thus, there is no need to go to the server 16, 82 in order to use the administrative tools 98 or to modify any of the settings in the client interface. Moreover, remote administration using the administrative tool 98 can be carried out in any of the various ways discussed further above.

Figure 10:
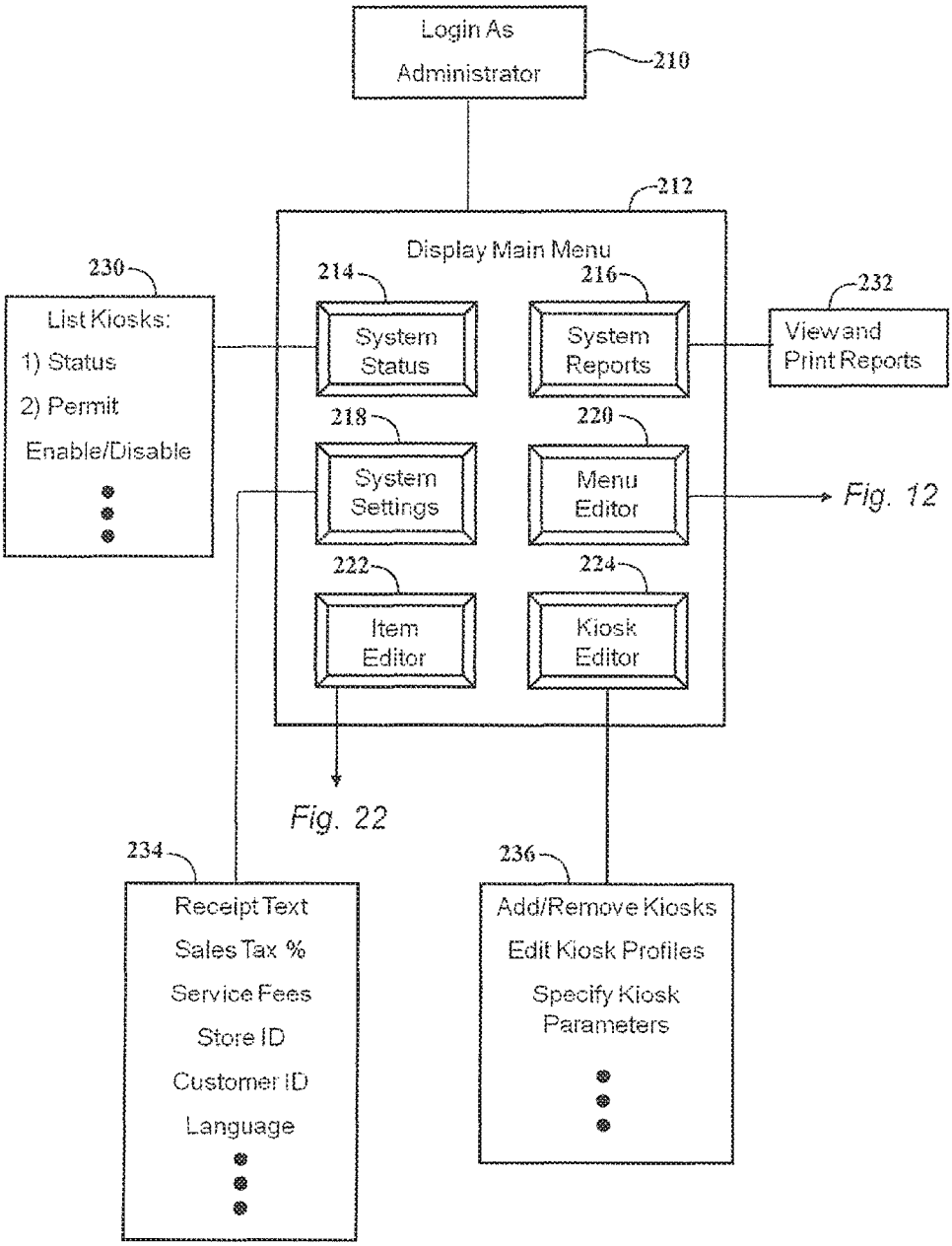
FIG. 10 illustrates the initial display screen of the administrative tool and also illustrates the main menu including selectable options.

FIG. 10 shows the initial step and display screen 210 upon launching the administrative tool process. The first step is to log into the administrative tool application which contains built in security that requires password access. Access to the tool is limited to persons with administrative or manager privileges. Kiosks may require administrators and managers to login by entering an ID or password using the touch screen, by swiping an ID card using the optional magnetic strip reader, by sensing an RFID tag, or any other suitable method of identification. The administrators have access to the full range of features that are available via the administrative tool, whereas the managers have access only to a subset of these tools. The manager access can be implemented by providing the various configurable items of the tool with a security parameter having two or more different possible values (e.g., administrator and manager) and then setting that parameter for each item depending upon whether or not manager access is desired. Thus, for example, the security parameter for disabling an item or changing the order of items on a screen can be set to "manager" so that both managers and administrators can disable an item or change the order of items on a screen, whereas the other attributes associated with an item (e.g., the display graphic and/or identifying text) can have their security parameter set to "administrator" so that only the administrator and not the manager can change these settings. The particular IDs assigned to individuals can be associated with either the manager or administrator security levels so that the user is given the proper access upon login.

When an administrator logs into the administrative tool the kiosk displays a main menu 212 with six options including: system status 214, system reports 216, system settings 218, menu editor 220, item editor 222, and kiosk editor 224. System status 214 lists the kiosks in the system (block 230) and enables the administrator to enable or disable any kiosk, control the volume level of any kiosk, turn on and off ordering access to alcoholic beverages, and view the kiosk's status (idle, in use, etc). System reports 216 enable the administrator to view and print sales reports (block 232) of any individual kiosk or all kiosks for a given day or time period. System settings 218 enable the administrator (block 234) to enter messages to print at the top and bottom of customer receipts, enter sales tax percentages, enter service fees, enter store ids, enter customer ids, and select available languages. System settings 218 also allow the administrator to create and edit day parting. Day parting automatically updates the items available for purchase on the client interface depending on the day and time of day. For example, if a restaurant wants to have separate breakfast and lunch menus, day parting will allow the administrator to define which days and times the breakfast and lunch menus are available. This allows the administrator to quickly modify the days and times when a menu of items is offered rather than having to make such changes to each item in the menu. The remaining three options on the main menu screen will be described in greater detail below.

Figure 11:
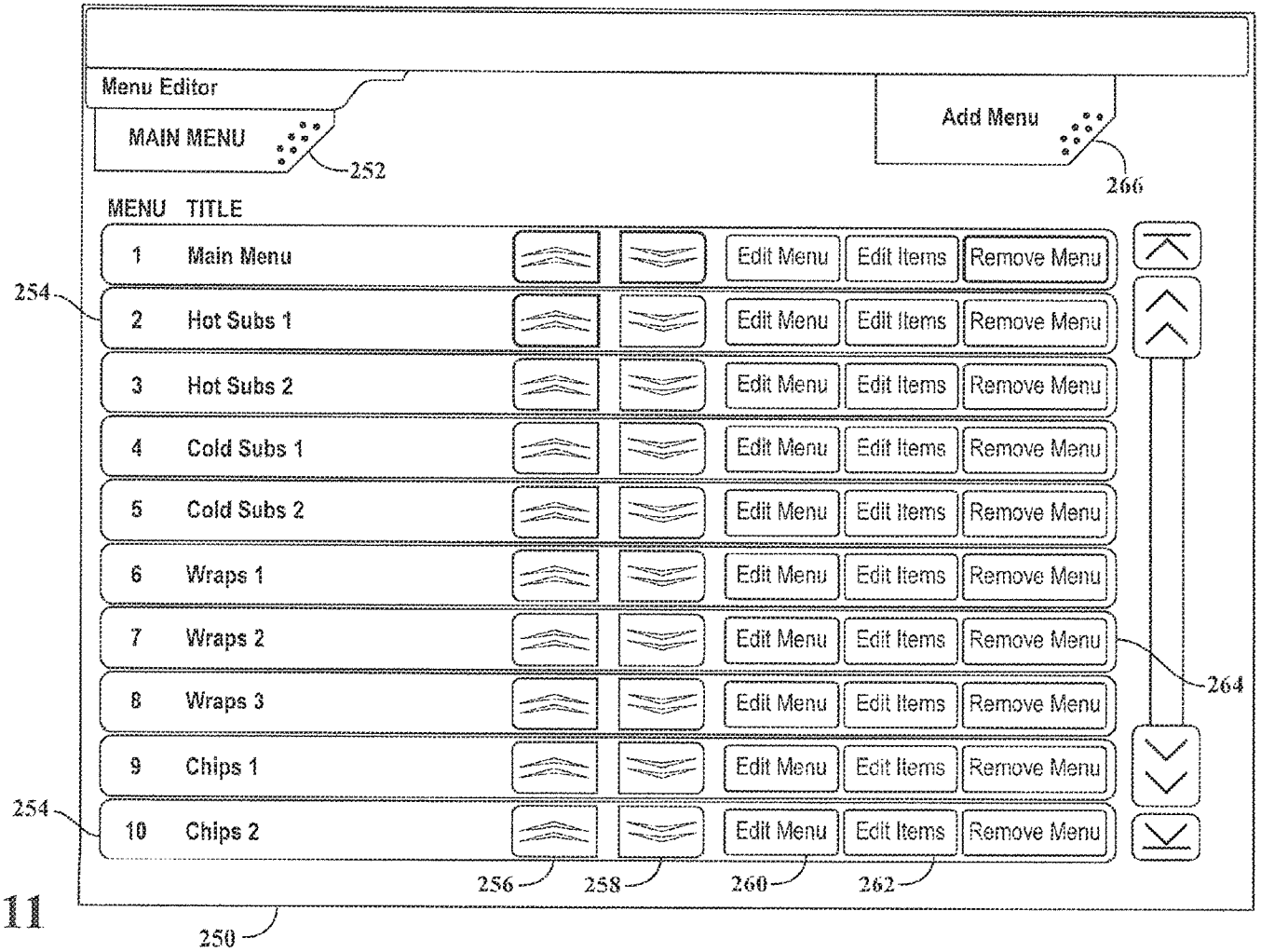
FIG. 11 depicts a menu editor screen of the administrative tool which allows an administrator to create and edit the screens or menus that customers see in the self-order application running on a kiosk.

Selecting "Menu Editor" 220 launches the menu editor shown in the screen 250 depicted in FIG. 11. The menu editor enables the administrator to create and edit the screens or menus that customers see. The main menu in the menu editor lists all menus and submenus 254 created for the client interface. The administrator may change the menu order on the list by touching up or down arrow buttons 256 and 258, respectively, next to any menu 254 (except the top/main menu) in the list. Note that the order on the menu editor does not correspond to the order that customers see the menus when placing an order, but merely allows the administrator to organize and group the menus in the editor. From the menu editor, the administrator can configure the overall look and content of each menu (via the menu edit button 260) and, for that menu, can edit the individual buttons to associate them with different items and options (via the edit items button 262). A menu is removed via the remove menu button 264.

Figure 12:
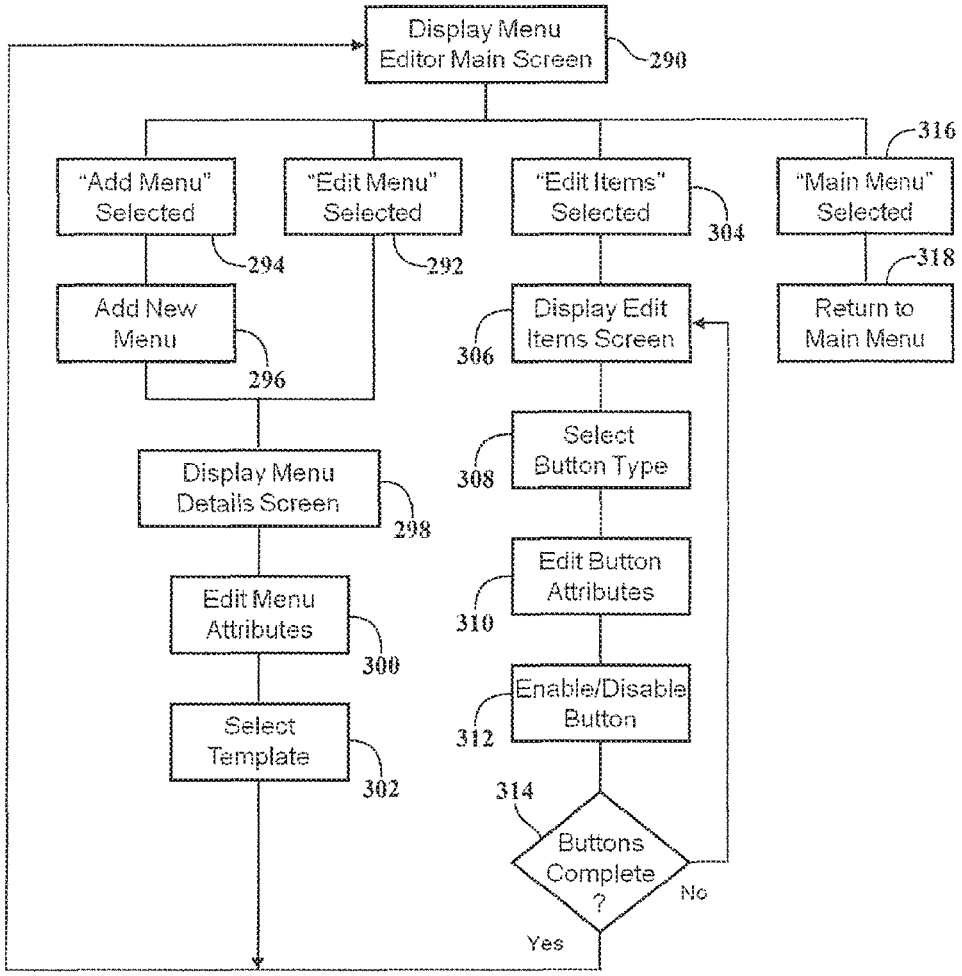
FIG. 12 illustrates a method of editing menus using the menu editor.
Figure 13:
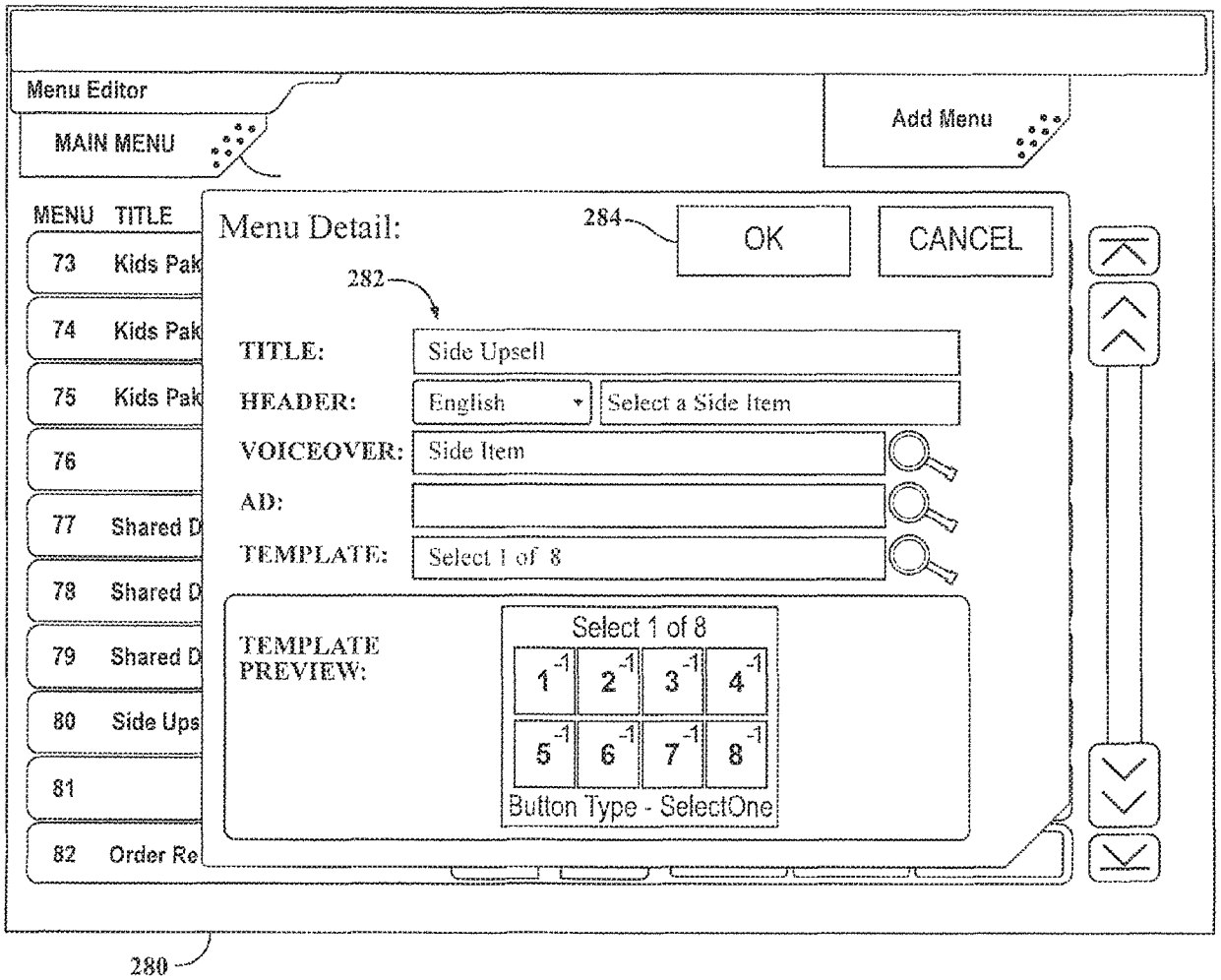
FIG. 13 depicts a menu details screen of the administrative tool which provides editable menu attributes including the menu's template.

FIG. 12 shows a method of editing menus using the menu editor. The displaying of the menu editor main screen is indicated at block 290. The administrator may edit any menu listed in the menu editor by selecting (block 292) the edit menu button 260 (FIG. 11) or may add a new menu by selecting (blocks 294, 296) the add menu button 266 (FIG. 11). Selecting the edit menu button 260 or the add menu button 266 launches (block 298) a menu details screen 280 such as is shown in FIG. 13. The menu details screen 280 provides several editable menu attributes 282 such as the menu's template, title, header text, language, voiceover, and advertisement. A voiceover is an audio file that plays when the menu is displayed, and an advertisement is a graphic, sound, or video/animation clip displayed on the menu. Several of the attributes are editable using only the touch screen, such as the voiceover or graphics, both of which can be selected from a stored library of media files that have either been downloaded to the client kiosk or are available from the local server or remote server. Other attributes require the administrator to add text to a field. The administrator may add text by using a pop up keyboard on the touch screen, a keyboard provided with (or temporarily connected to) the kiosk, or through voice recognition. The header is used during ordering to provide instructions to a customer for the menu (e.g., "Select a Sandwich"). In FIG. 12, the editing of menu attributes is indicated at block 300 while the selection of a template is indicated at block 302.

The primary components of each menu screen are buttons that allow the customer to make selections among available items and options. Buttons can be directly added one at a time by the administrator from an available collection of different buttons when building the screens. Alternatively, and as used in the disclosed embodiment, templates containing predefined groupings of buttons are used to develop the menu screens. These templates are menu layouts that assist administrators in creating and modifying menus quickly and with little effort. Several template examples are shown in FIGS. 14-19. The templates define the overall layout of the menu such as the number and types of buttons, and placement of buttons, title, heading, and ads. By simply selecting a template for a menu, the administrator determines the number of buttons a customer sees on the menu, what happens when a customer selects a button (recall that each type of button has unique behavior), and the overall appearance of the menu. The use of templates eliminates the need for administrators to write their own code to develop the layout and behavior of the menus.

Figure 14:
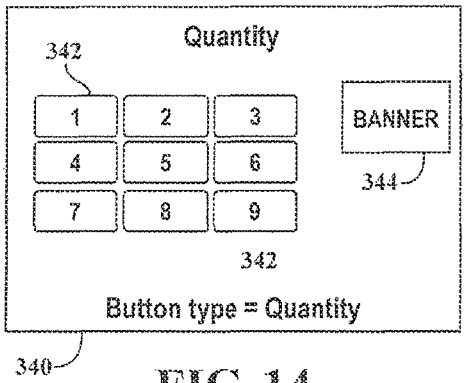
FIG. 14 shows a Quantity menu template.

FIG. 14 shows a Quantity template 340 available in the administrative tools. The Quantity template 340 allows customers to enter the quantity of an item to add to their order. The template 340 includes a series of buttons 342 with corresponding numbers associated with them to enable customers to select the desired quantity. The number of buttons 342 and their corresponding numbers are configurable so that quantities may be restricted such as for the sale of alcoholic beverages. The template 340 also includes standard features such as a title and a banner 344 for displaying an advertisement or image on the template 340. The customer is taken to the configured "next menu" when the selection is made.

Figure 15:
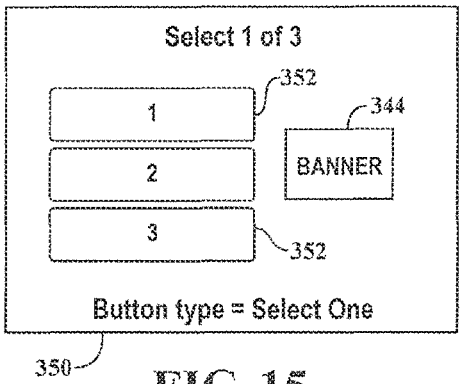
FIG. 15 shows a Select 1 of 3 menu template.

FIG. 15 shows a Select 1 of 3 template 350 that is used to allow the customer to pick one of three different choices. Once this template 350 is chosen for a particular menu, the individual buttons 352 for the menu can be configured with graphics, animation, and behavior (e.g,, how the system responds to the button being pressed) using the "edit items" selection 262 in the administrative tool's menu editor (FIG. 11). As noted at the bottom of this menu template 350, the default button type is the SelectOne button which is described above. For any particular template, there may be multiple types of buttons that can be used, and the available types will be selectable by the administrator during setup of the menu. For the Select 1 of 3 template 350, MenuButtons are available for use in addition to the SelectOne buttons so that the template can be used to navigate to sub-menus without any particular item being selected.

Figure 16:
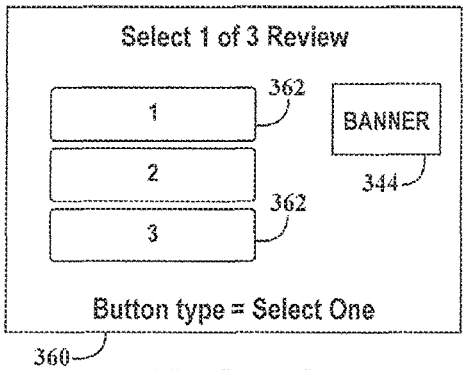
FIGS. 16 shows a Select 1 of 3 Review menu template.

FIG. 16 shows a Select 1 of 3 Review template 360. This template 360 is intended to be placed at the end of the customer's order to provide customers a chance to view and edit their orders. The template 360 includes three select review type buttons 362 along with a title and a banner advertisement 344. The select review buttons 362 are used to list each item in the order, its price, and an option to cancel the item. Whereas most templates have button types that can be selected by the user, the content of the review buttons 362 of this template is automatically generated and cannot be edited by the administrator. Thus, in addition to having different types of buttons, the system includes some button types that are configurable, and others that have predetermined behaviors and that have dynamically generated content based on the customer's order. A separate review button 362 is used for each item in the order, and the actual number of review buttons 362 shown during an order may be dynamically generated on the menu based upon the number of items in the order. Thus, where there are more than three of these buttons, as indicated by the template, a vertical scroll bar or up/down scroll buttons can be added by the system to the screen display to allow the customer to scroll up and down among the various review buttons.

Figure 17:
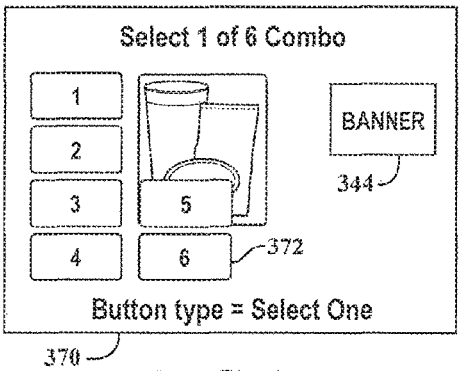
FIG. 17 shows a Select 1 of 6 Combo menu template.

FIG. 17 shows a Select 1 of 6 Combo template 370. This template 370 includes a title and a background image detailing a category of items for selection, such as a combination meal. The customer is immediately taken to the next menu when they select one of the six SelectOne or MenuButtons 372 that are available for use with this template.

Figure 18:
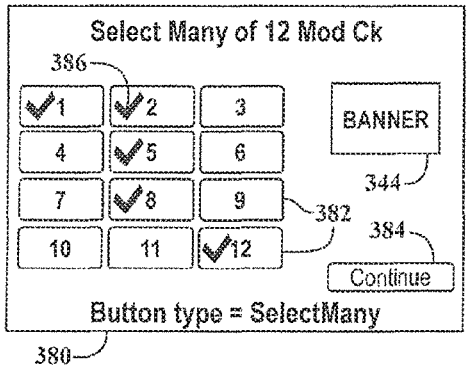
FIG. 18 shows a Select Many of 12 Modifier Check menu template.

FIG. 18 represents a Select Many of 12 Modifier Check template 380. This template 380 includes a title, banner 344, and twelve MultipleMod buttons 382 and a continue button 384. The template 380 allows customers to select options to a previously selected item from the twelve select MultipleMod buttons 382. Each button 382 appears with a check mark 386 on it when selected. Selecting a button 382 having a check mark 386 deselects the button 382 and the check mark 386 is removed. The customer selects the continue button 384 when all selections are complete to jump to the next menu.

Figure 19:
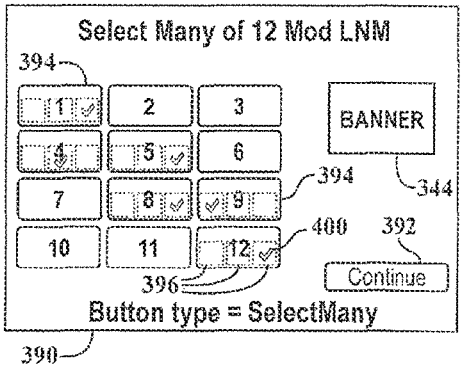
FIG. 19 shows a Select Many of 12 Modifier Less/Normal/More menu template.

FIG. 19 shows a Select Many of 12 Modifier Less/Normal/More template 390. This template 390 contains a title, a banner 344, a continue button 392, and twelve LNM buttons 394. This template 390 allows customers to select multiple options (e.g., toppings) to a previously selected item and then specify the relative quantity (less/normal/more) by selecting from one of three sub-buttons 396 on a LNM button 394. Alternatively, none/normal/extra (NNE) buttons can be used on the template 390 to allow the customer to select multiple modifications to the item by selecting from none, normal, or extra on a single button. A check mark 400 appears on the buttons when selected. SelectOther buttons can also be used on this template 390 to select multiple items or options on the menu with a single button touch. The customer presses the continue button 392 when finished to jump to the next menu.

Thus, as will be understood by those skilled in the art, the system provides a group of templates (with FIGS. 14-19 being examples) with each template having a group of buttons organized into a particular arrangement, with the buttons being of one or more different types (i.e., having different behaviors when pressed). In some cases, two templates may differ only by the number of buttons presented. For example, the Select 1 of 12 Modifier Check template 380 of FIG. 18 has twelve buttons arranged in a 3×4 array, and the system can also contain a select one of eight (buttons in a 2×4 array) or a select one of fifteen (3×5 array). In other cases, templates may differ only by their button types (compare the templates 380 and 390 of FIGS. 18 and 19, respectively).

Figure 20:
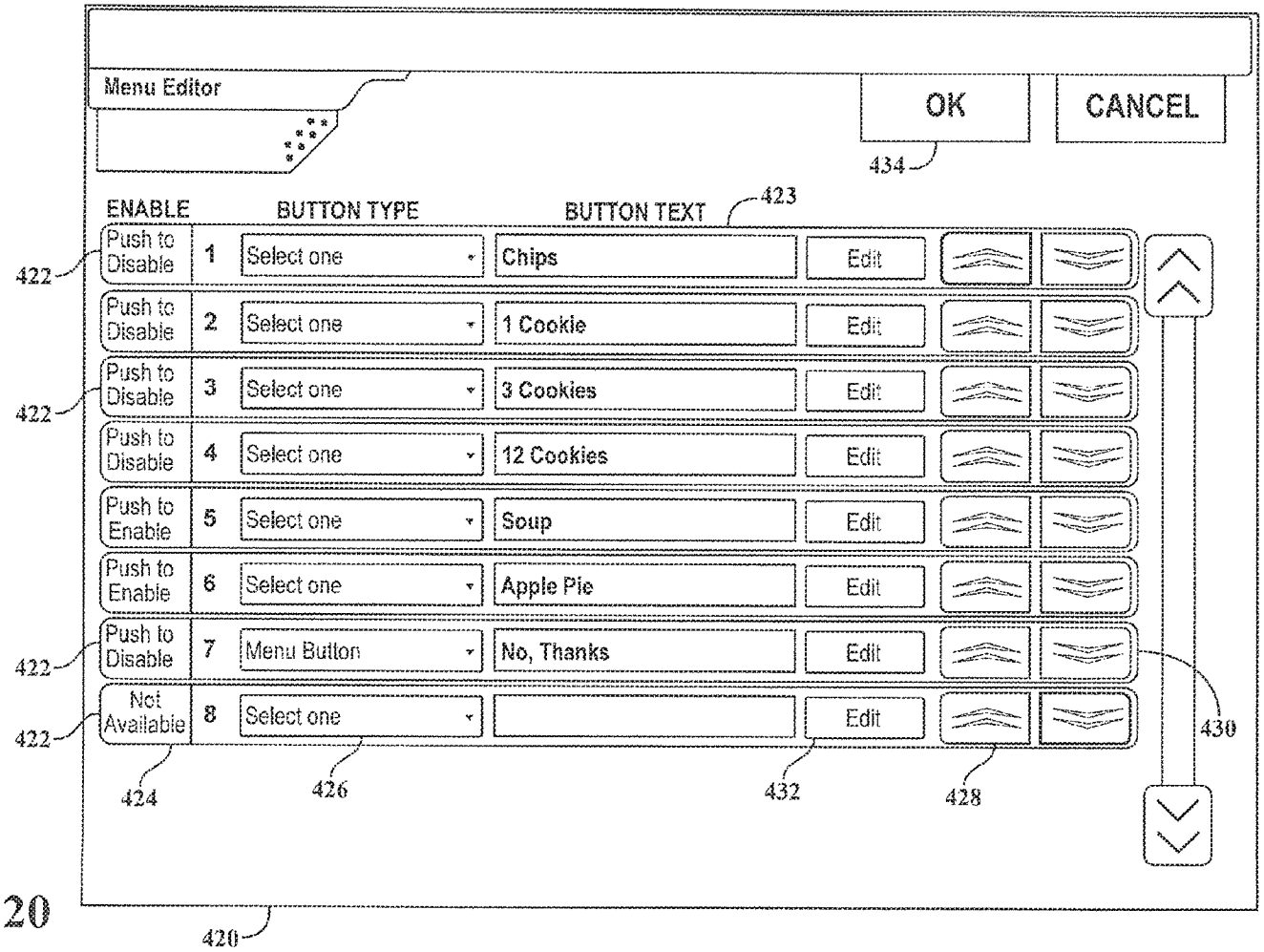
FIG. 20 depicts an edit items screen of the administrative tool which enables the editing of characteristics of each individual button on a menu.

Referring to FIG. 12, once the administrator edits the menu attributes (block 300), including selecting a template for the menu (block 302), and then saves the changes (OK button 284, FIG. 13), the program returns to the main menu screen 250 shown in FIG. 11. To then edit the individual buttons and associate them with food items and options and associated button text, graphics, voiceovers, and button behaviors, the administrator selects the "edit items" button 262 next to the menu 254 being set up. This enables the administrator to edit the characteristics of each individual button on the menu. The administrative tool displays an edit items screen 420, depicted in FIG. 20, having a list of buttons 422 and their title 423 for the selected menu. The administrator has the option to enable or disable any individual button (button 424), change the button type if desired (pull-down list 426), and arrange the button order (up and down buttons 428 and 430, respectively). In particular, the administrator normally will first select a button type and then touch "edit" 432 next to the button to open a list of attributes for that button.

The administrator can modify each button attribute in the editor. The list of attributes varies depending on the button type. Some attributes include: the title of the button, the item/product associated with the button, the image(s) overlaid on the button, the quantity of items, pricing options for the item associated with the button, and selecting a day part for the button. The title can be entered in different specified languages so that the customer can be given the option of specifying a language at which point all wording and titles change to the specified language. The menu also enables the administrator to select which menu to activate when the button is selected on the touch screen. Selecting which menu to activate when each button is pressed creates a hierarchy of menus to guide the customers through the order process.

For example, the top menu in the self-order application may ask the customer to select a food category such as sandwiches, drinks, or sides. When selected, the sandwiches button activates a menu containing a number of sandwiches from which to choose. (The sandwich menu is the next menu to activate when sandwich category button is pressed.) Each button on the sandwich menu then activates a corresponding menu to allow the customer to choose or modify ingredients for the particular sandwich chosen. When the administrator has finished configuring the button attributes and which menu to activate on the button, the administrator is brought back to the edit screen 420 of FIG. 20. Individual buttons can also be enabled or disabled on this screen (button 424). This allows, for example, a button for a food item or option to be setup and then temporarily disabled in the event that the item or option becomes unavailable. When the administrator has completed editing the buttons for a particular menu, the process returns (OK button 434) to the menu editor (FIG. 11). After creating and editing all necessary menus, the administrator selects the Main Menu button 252 on the menu editor screen 250 and is returned to the main menu 212 shown in FIG. 10.

In FIG. 12, the process flow is depicted by block 304 (selecting "edit items" button 262 in the menu editor main screen 250 of FIG. 11), block 306 (displaying edit items screen 420 of FIG. 20), block 308 (selecting the button type from pull-down list 426), block 310 (edit button attributes by selecting edit button 432), block 312 (using enable/disable button 424), block 314 (selecting OK button 434 when button editing is completed to return to the menu editor main screen 250 of FIG. 11), block 316 and block 318 (selecting Main Menu button 252 on menu editor main screen 250 to return to main menu 212 of FIG. 10).

Figure 21:
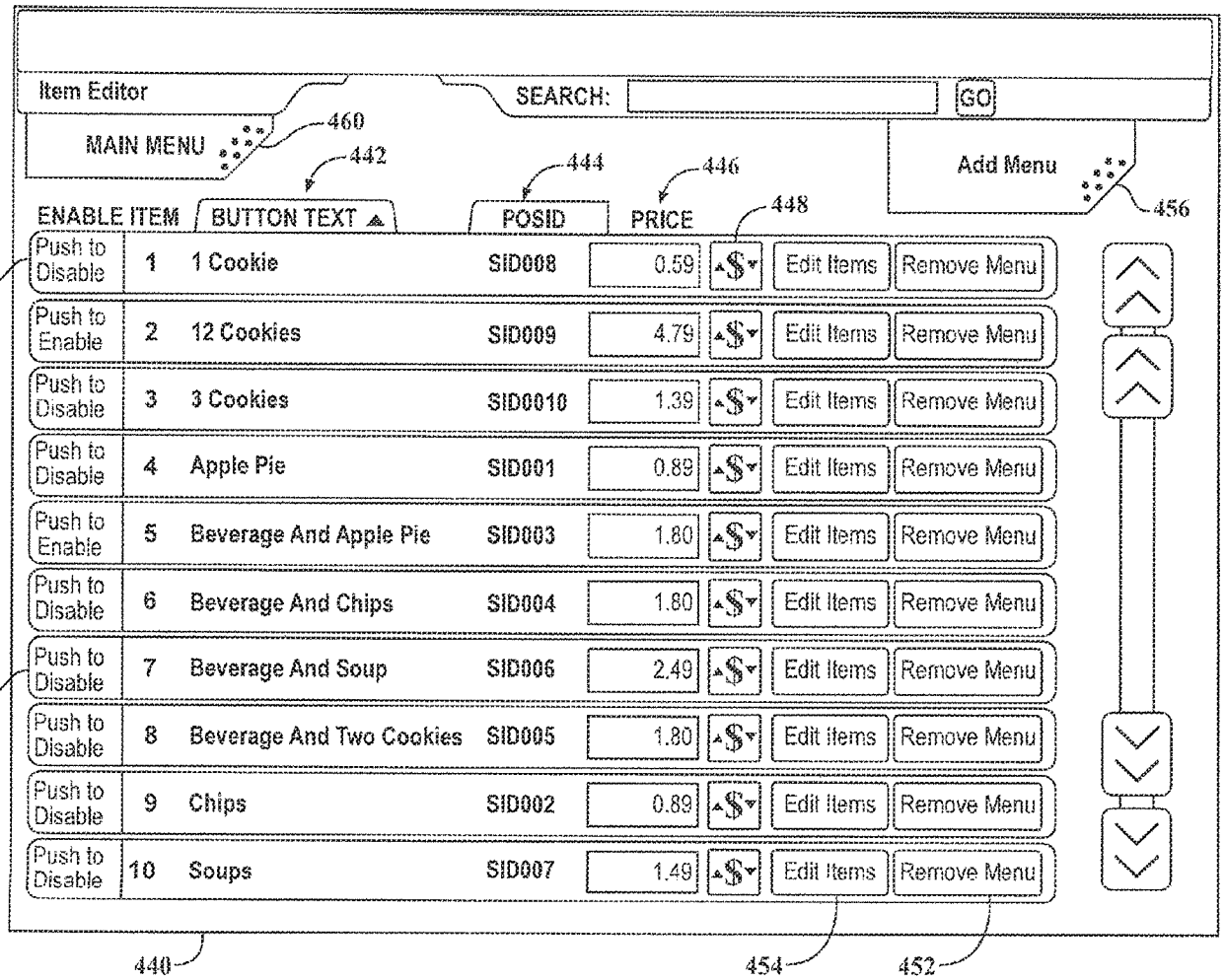
FIG. 21 depicts an item/product editor screen of the administrative tool which enables the editing of the individual items/products for sale.
Figure 22:
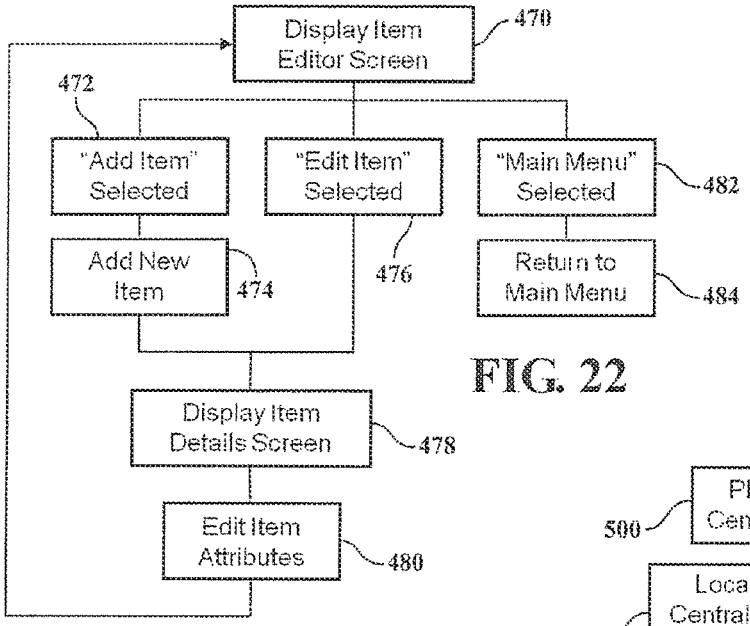
FIG. 22 illustrates a method of editing items/products with the item/product editor.

The individual items or products available for sale are edited in the item editor which can be selected using the Item Editor button 222 on the main menu 212 of FIG. 10. FIG. 21 depicts the item editor screen 440 and FIG. 22 is a flowchart illustrating one example of how to configure the various food items and options using the item editor. In screen 440 of FIG. 21, the items are listed with their button text 442, an ID 444, and a price 446. A button 450 next to each item listed enables or disables the item on the client interface. When disabled, the item cannot be associated with a button under the menu editor. The price of each item is displayed and is editable through a text field or through price increase or decrease buttons 448 next to the text box. A "Remove Item" button 452 allows the administrator to entirely remove an item from the system. The administrator may edit an item by selecting "Edit Item" 454 next to the item listed, or add an item by selecting "Add Item" 456 on the menu. When adding or editing an existing item, the administrative tool launches a separate items detail screen with multiple tabs to edit various item attributes. The tabs include a text tab, detail tab, recipe tab, and UDF tab. The text tab provides text fields to define the text used to identify the item (again, different language versions of the same text can be entered), the text to be listed for the item on receipts, and the text to be listed for the item on the kitchen build. The detail tab provides fields to edit the item's ID, price, image, type (product or option), day part, build group, and other miscellaneous characteristics such as if the item is part of a meal, sold as a unit, heated, can be upsold, etc. The recipe tab allows the administrator to define the ingredients used to make the item. The UDF tab includes general purpose, user defined fields for customers to use. In one example, the UDF tab allows the administrator to enter nutritional information for the item for display on the client interface and/or the customer receipt. When the administrator has completed editing attributes, the item editor screen 440 is displayed again on the kiosk. Once the administrator has completed adding and editing items, the Main Menu button 460 can be selected to return to the main menu 212 of FIG. 10.

In FIG. 22, the process flow for using the item editor is depicted. The item editor screen 440 (FIG. 21) is displayed at block 470. Blocks 472 and 474 depict adding a new item by selecting add item button 456 (FIG. 21), while block 476 depicts editing an existing item by selecting edit item button 454 (FIG. 21) for one of the existing items. When editing an existing item or adding new item, block 478 indicates that the item details screen is displayed. This screen allow the editing of various item attributes, as indicated at block 480. Once the adding and editing of items is completed, blocks 482 and 484 depict selecting Main Menu button 460 (FIG. 21) and returning to the main menu 212 of FIG. 10.

The last main menu option on the main menu 212 (FIG. 10) of the administrator tool is the kiosk editor (button 224). The kiosk editor allows the administrator to add client kiosks to the system (block 236). Each kiosk is given a name, an IP address, background images, and an attract loop. The attract loop is a video or animation that is played when the kiosk is not in use and is intended to attract customer attention. The kiosk editor also allows the administrator to select a kiosk type or profile. Kiosk profiles allow administrators to define basic modes of operation for the kiosk. For example, most kiosks are typically located within stores and have a "local" profile telling customers where they should pay locally (nearby) for the order. Other local kiosks may enable customers to pay at the kiosk through a credit card, debit card, or other methods and so may define a "local pay" profile. Others may include sales tax and have a local tax profile. Likewise, kiosks located outside of a store, such as within a shopping mall or park may require a separate profile to inform customers where to pick up their orders. It will be obvious to one skilled in the art that many other types of profiles are possible to suit the needs of a particular system.

The administrative tool saves all changes to the server after the administrator has made all desired changes to the customer interface using the administrative tool. Upon exiting the administrative tool, it prompts the administrator to save the changes or discard changes. All media and configurations of menus, items and options are saved on the server kiosk, and the server updates each client connected to it with the corresponding saved changes when each client is idle. This can be carried out by pushing the configuration changes from the local server to each client kiosk, or by programming of the clients to periodically check for new configurations, such as by using predefined time intervals and/or during idle time when the kiosk is not in use. The programming needed for carrying out these approaches to updating of the clients will be apparent to those skilled in the art.

Media updates of new graphics, voiceovers, videos, animations, and the like that are used for building the menus and screen displays can be handled similarly to updates of the menu configurations. The new media can be placed on the server kiosk and then pushed to the client kiosks, or the clients can periodically check for new media using version numbers, unique filenames, timestamps, or other means of identifying new files, as will be known to those skilled in the art. Using this approach, the server updates the clients by storing the media in a media folder on each client. Alternatively, new media can be cached at the server to update the client only when each client needs to use the updated file(s), in which case the media need not be stored in non-volatile memory at the local client kiosks.

Figure 23:
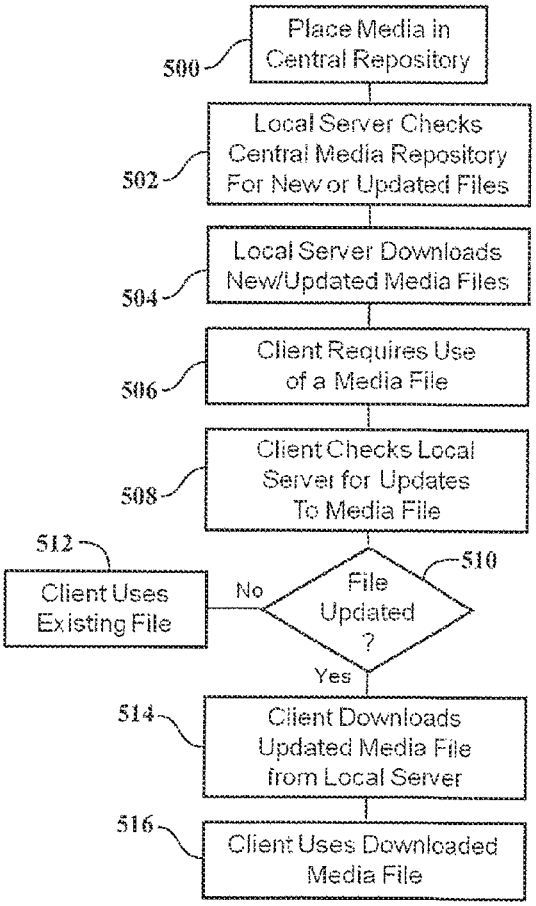
FIG. 23 illustrates a method of updating local servers and clients with a common set of media from a central server.

In an alternative embodiment, the remote server such as the central server 22 of FIG. 1 provides a method for updating multiple servers with a common set of media as shown in the process of FIG. 23. The remote server provides a centralized media repository for multiple local servers. The centralized media repository stores all necessary media for the local servers associated with the remote server. When a new media file is available, the administrator stores the media file on the remote server in the centralized media repository (block 500). Each local server synchronizes its media with that of the centralized media repository so that any changes to the repository are downloaded to each local server either upon triggering from the remote server or as the result of periodic checking by the local servers (blocks 502, 504). The local servers then update each client kiosk with the media files when each client is idle. This can be done by programming the client kiosks with an update function that checks with the server during each period of inactivity of the kiosk. Alternatively, the client may check the local server to see if a new media file is available whenever a particular client kiosk needs to use the file for the self-order application (blocks 506, 508, 510). If a new file is not available, the client uses an existing file (block 512); if a new file is available, the client downloads and uses the new file (blocks 514, 516).

For example, a new advertisement can be placed in the media repository on the remote server. Each local server recognizes that a new media file is available when each local server periodically checks the repository for updates. Recognition of new media can be done using, for example, a timestamp associated with each media file and the local servers can then download any media having a newer timestamp than that for their most recent prior download. The local servers download the new files into the local server media folder. The next time each client is activated to display a particular advertisement on a particular screen display, it pulls the new advertisement from its local server, uses the advertisement on the kiosk display, and if desired, caches it into memory for subsequent use. In this way, each local server kiosk maintains a local master copy of the media which is then accessed as needed by the local clients. Furthermore, by at least in part using vector graphics files, all media can be stored on the server and not the client kiosks and then just accessed as needed during operation.

The remote server also provides methods for updating local servers and clients with other features. For example, new templates can be provided to allow more menu configuration options. Where the templates contain specific functionality/behavior that is not already provided for by the self-order application software as a configurable item, the software on the kiosk can be pre-configured to accept and process the new templates to incorporate their functionality into the software. Where the templates involve only layout of existing objects contained within the software system, they can be downloaded and stored in memory in the same manner as media updates.

Figure 24:
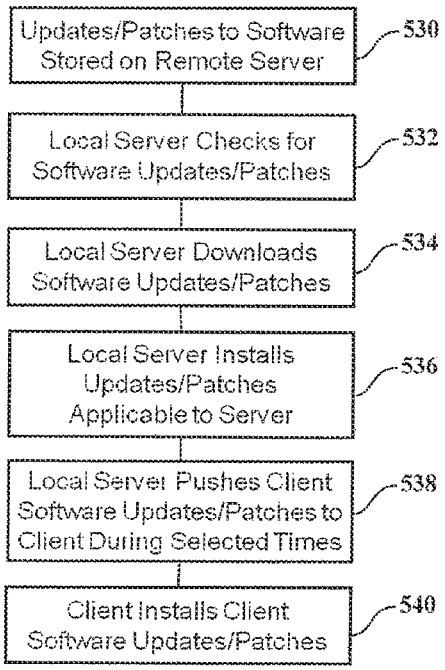
FIG. 24 illustrates a method of updating software on and providing software patches to local servers and clients from a remote server.

As another example, the system includes the ability to perform software updates to either add new functionality or as patches to improve or fix existing software. This software updating can be carried out using the process shown in FIG. 24. Software updates and patches are initially stored on the remote server (block 530). Local servers check the remote software for software updates and patches, preferably during periods of little or no customer activity (block 532). The local server downloads the updates and patches stored on the remote server (block 534). The local server installs the dates and patches that apply to the software running on the local server (block 536). Administrators can choose when to download and install the updates and patches to ensure that installation does not interfere with customer use. Likewise, updates and patches that apply to the clients are pushed to the clients from the local servers and are installed on the clients during inactive periods or at times selected by the administrator (blocks 538, 540).

Apart from using the Internet for online ordering and centralized storage and distribution of menu configurations, media, and software, it can also be used by the administrators to access the administrative tools remotely using a standard web browser, rather than having to use a kiosk. The web server on the local kiosk server includes either a web-enabled version of the administrative tool or includes a separate web services process that provides a web interface into the server process that allows configuration of the self-order application in the same way as the administrative tool. Like the web client, the web enabled administrative tool reduces overhead by using vector graphics. The web enabled administrative tool also enables store owners to update multiple servers from a single location, for example, by logging in and updating the local servers either one at a time or as a group. This feature can be used to update any of the items noted above—menu configurations, media updates, templates, software enhancements and patches.

Figure 25:
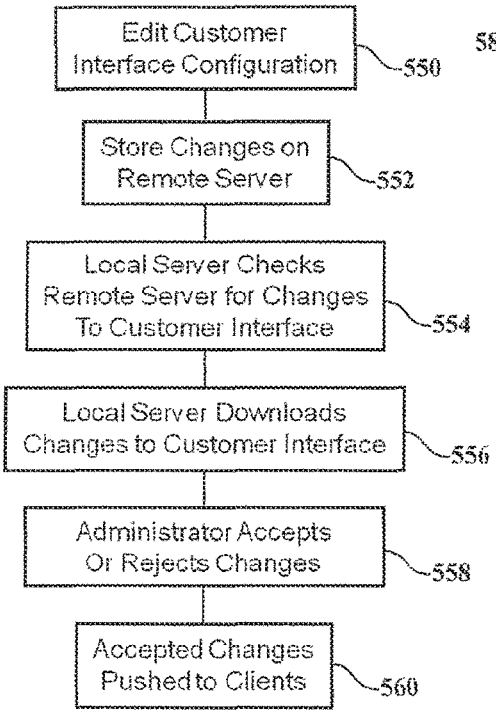
FIG. 25 illustrates a method of remote administration of local servers and clients to edit the customer interface configuration.

The remote server can be used for store owners, franchisees, etc. to update multiple local servers, such as at multiple store locations, from one central location. By tracking the IP addresses or names of each local server registered with the remote server, all local servers can have updates happen from the central location, eliminating the need for administrators to make the changes at each local server individually. FIG. 25 illustrates one example of one method of updating local servers. For instance, a franchiser can create a new item or modify an existing item with all of its associated attributes and save it to the remote server (blocks 550, 552). This can be done, for example, by using the administrative tool on the remote server to configure the menus and items locally stored there. As previously described above, each local server associated with the remote server can synchronize itself with the information stored on the remote server, and this can be done by having the local server check for changes to the configuration of the self-order application, or the remote server can automatically send the changes to the local server (blocks 554, 556). In the event that not all store locations are intended to use the same menus or pricing, then the changes can be sent to less than all stores and/or local servers. If desired, the administrator of each local server can be given the option to accept or reject each change on each local server using the administrative tools (block 558). Accepted changes can then be updated on each client registered with the local server (block 560).

Figure 26:
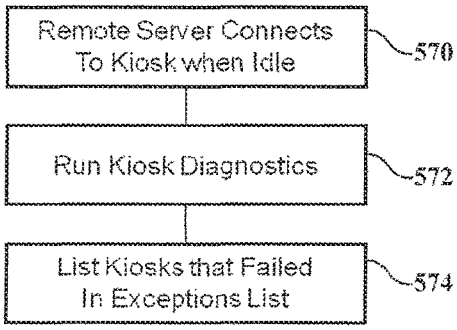
FIG. 26 illustrates a method of remotely diagnosing a kiosk.

The remote server also provides a method of remotely diagnosing a kiosk to prevent downtime as seen in FIG. 26. During periods when the kiosk is idle, the remote server connects to local servers and/or client kiosks to run a diagnostic of each kiosk (blocks 570, 572). The diagnostic verifies that each kiosk is running properly and contains the core files necessary to function. Kiosks that fail the diagnostic are listed in an exceptions list to alert administrators that there is a potential problem (block 574). Most issues can be resolved remotely using the administrative tools and thus avoid downtime of the kiosks. In some situations, due to firewall issues, diagnostics may be conducted by recording information locally and then uploading information to the remote server.

Figure 27:
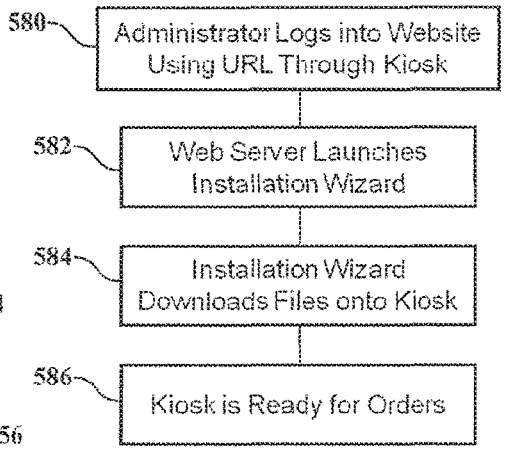
FIG. 27 illustrates a method of installing a new kiosk (or restoring a kiosk) using a web installation service provided by a remote server.

The remote server also provides a method of simplifying installation of a new kiosk or restoration of a kiosk after a catastrophic failure. To install a new kiosk or restore a previously working kiosk, an administrator simply needs to access a web installation service provided by the remote server as seen in FIG. 27. The administrator accesses the installation service by connecting to a URL using the kiosk (block 580). Next, the administrator logs in to the installation service to verify their credentials. Once the service verifies the credentials, the web service takes the administrator through an installation wizard that loads all necessary files onto the kiosk, including any software, database, menu, configuration files and media necessary for use (blocks 582, 584). At the completion of the wizard, the kiosk is ready for use (block 586). The particular menu and item configurations already setup for another local kiosk can be accessed from the server and used for the new or restored kiosk.

Other methods of automatically identifying kiosks that need restoration may be used. For example, the remote server can automatically identify kiosks in need of restoration. The remote server stores the IP addresses and kiosk names of all kiosks registered with the remote server. Assuming that the kiosk maintains its IP address and can connect to the Internet after failure, the remote server can identity the kiosk. By running a diagnostic on the kiosk, the remote server can identify that the kiosk requires restoration and begin the installation service. As an alternative to running a diagnostic, kiosks can send a distress message to the remote server. Kiosks can detect their own failures through log files on the kiosks. Repeated error messages in the log files inform the kiosk that it requires restoration and inform the kiosk to send a distress message to the remote server. The distress message notifies the remote server to begin the installation wizard with the kiosk in distress.

Likewise, the remote server can recognize new kiosks by naming the new kiosk the same name as a replaced kiosk, assigning the new kiosk the same IP address as a replaced kiosk, or registering the new kiosk with the remote server by providing a name and IP address. Again, running a diagnostic on the new kiosk informs the remote server that the kiosk requires installation and triggers the installation wizard. After the wizard is complete, the new kiosk is able to receive orders.

Similarly, the installation wizard can use various methods to install or restore kiosks. The installation wizard can install the necessary files on the client or local server from the remote server. Alternatively, for a client, the installation wizard can download the necessary files onto a local server where the client is registered. The client then installs the necessary files from the local server, rather than the remote server. This method works particularly well when multiple clients registered with a local server require installation or restoration. Storing the necessary files temporarily on the local server reduces the overhead on the remote server and allows it to be available for other locations in need of its services. An alternative to downloading a group of necessary files is to download a ghost image on the kiosk. The ghost image runs on the kiosk after the download is complete and provides the kiosk with the complete contents of a hard disk needed by the kiosk.

Figure 28:
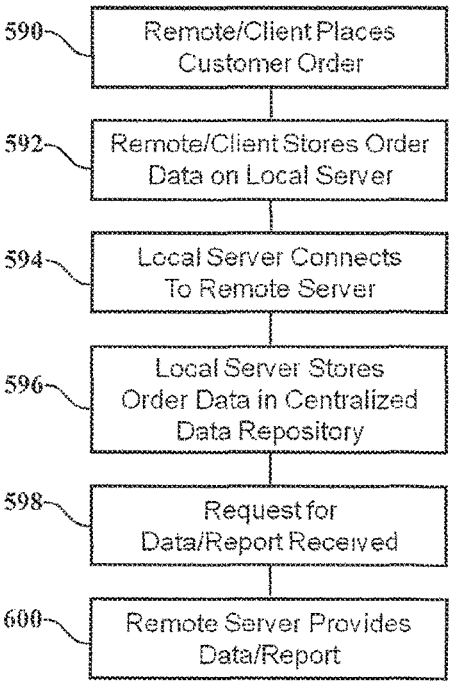
FIG. 28 illustrates a method of using a remote server to provide a central data repository for customer and/or order data, and to provide consolidated reporting.

Additional features of the remote server are to provide a central data repository for multiple local servers and provide a reporting module. The centralized data repository stores local transaction data from kiosks as well as customer data for use with customer recognition and recommendations. The reporting module combines data from client orders and remote client orders for consolidated reporting and graphing. As seen in FIG. 28, customer data and/or order data is stored on the local server when a customer places an order through a client or remote client (blocks 590, 592). The local server connects to the remote server periodically and stores the customer and order data in the centralized data repository (blocks 594, 596). Administrators request data or a report from the remote server that then supplies the data or report requested (blocks 598, 600). The consolidated reporting allows a store owner or corporation with multiple locations to run reports across multiple locations to show popular products, store performance comparisons, trends over time, etc. The reporting module also contains an export function to export raw data for analysis in third party tools.

Figure 29:
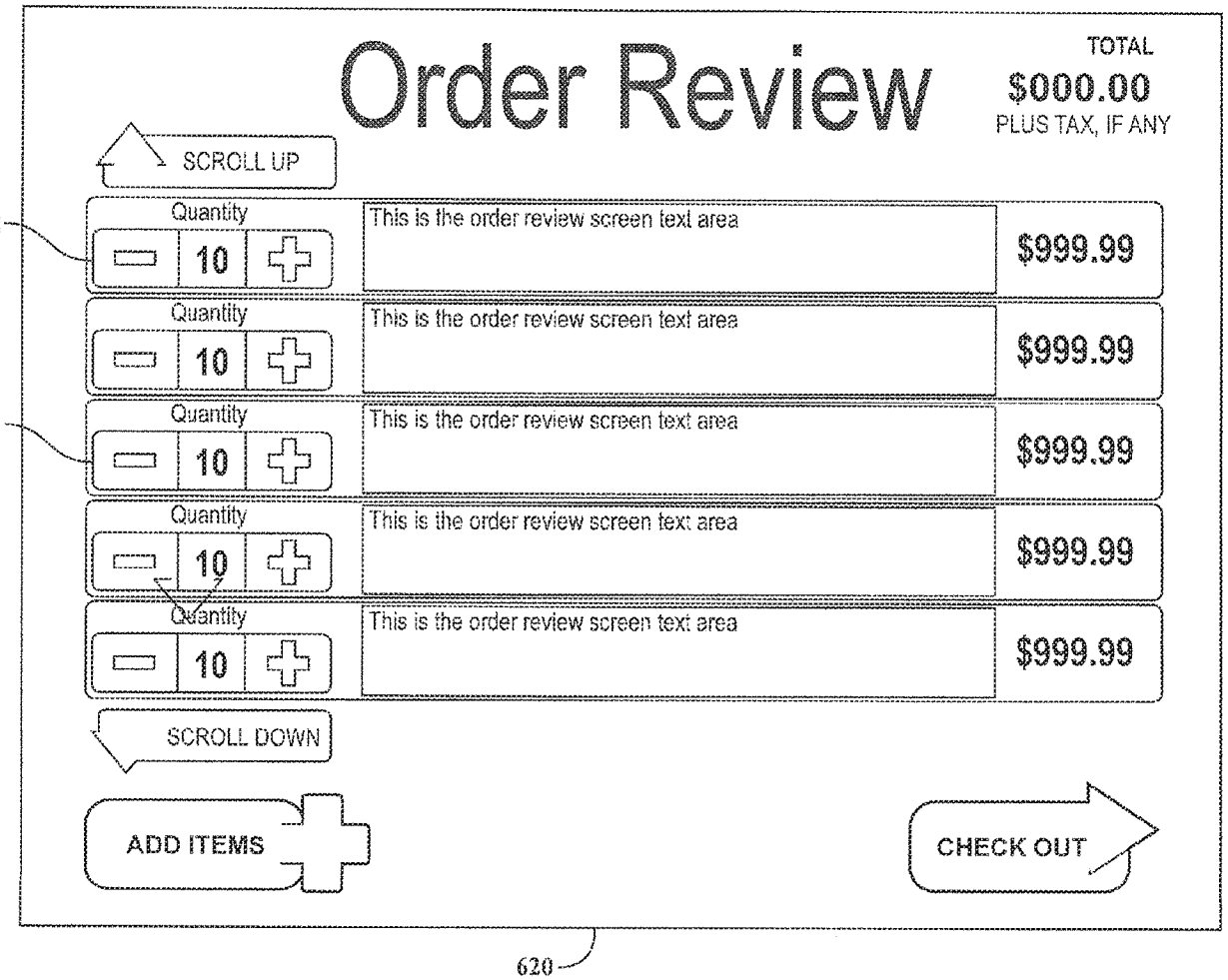
FIG. 29 illustrates an alternative order review template.
Figure 30:
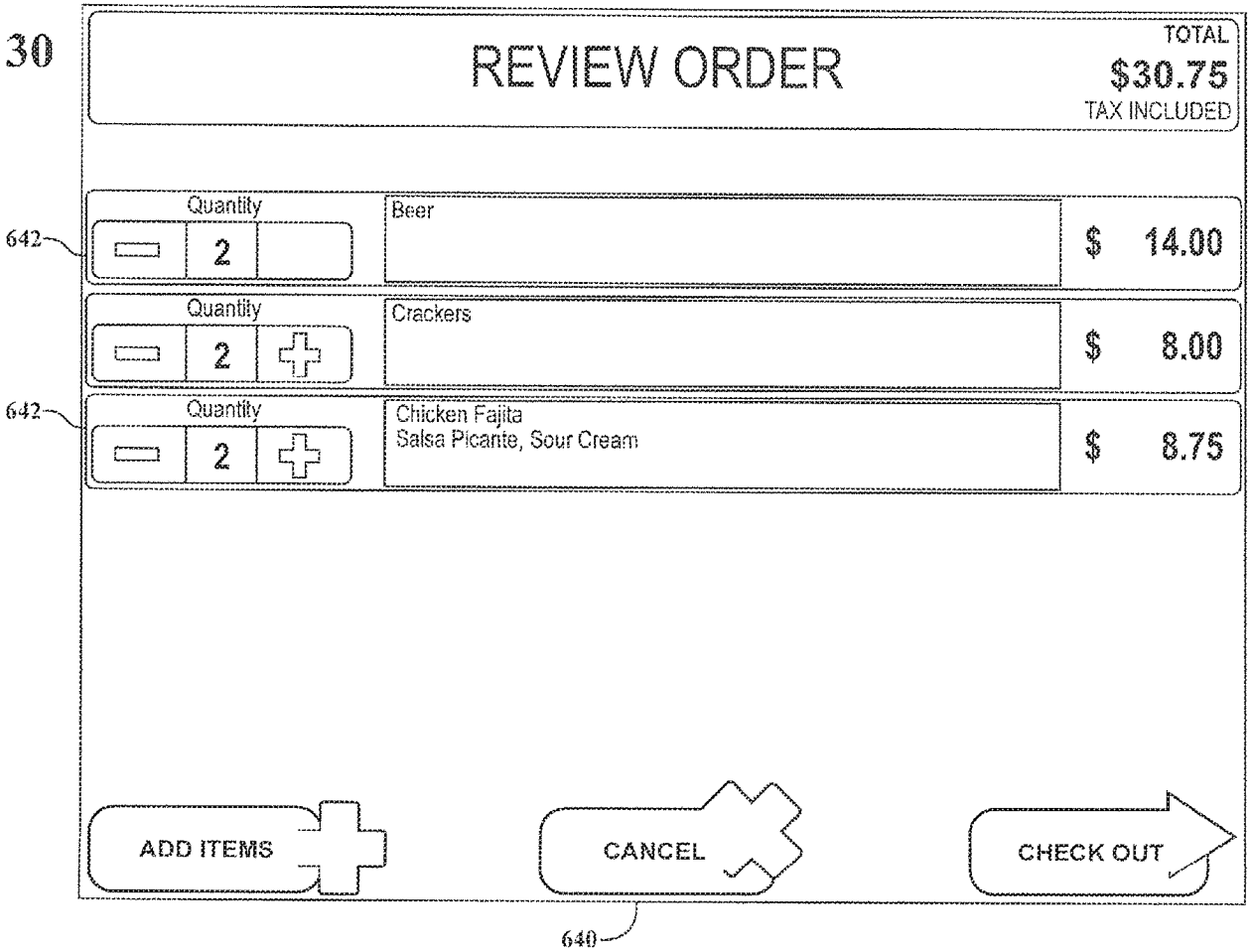
FIG. 30 illustrates the resulting screen display for the alternative order review template of FIG. 29.

It will thus be apparent that there has been provided in accordance with this invention a point of sale system for ordering an item that achieves the aims and advantages specified herein. It will, of course, be understood that the forgoing description is of preferred exemplary embodiments of the invention and that the invention is not limited to the specific embodiments shown. Various changes and modification will become apparent to those skilled in the art and all such changes and modifications are intended to be within the scope of this invention. For example, although the disclosed embodiment is a system particularized for use in quick-service chain restaurants, the invention is useful for a variety of different types of customer ordering of goods and services; for example, ordering concessions at entertainment venues, ordering of tickets for movies, theme parks, and/or sporting or entertainment events, car rental and other such reservation systems. Other such applications will become apparent to those skilled in the art. As one example, FIGS. 29 and 30 show respectively an order review template 620 (FIG. 29) and resulting screen display 640 (FIG. 30) as they might be used for concessions (ala carte) ordering at a sports entertainment venue. This template 620 uses yet another type of Quantity button 622 that displays + and – sub-buttons with a count between the buttons. The customer can then select the items and quantity they want and, then when at the order review, just prior to final acceptance, the customer is given an opportunity to make final adjustments to quantity (button 642). If desired, the system can be designed so that the template also contains buttons that provide the user an option to go back and modify an item (e.g., specify different toppings) or remove it altogether from the order. This can be done by adding appropriate button(s) next to each item. For modifying an item, a modify button can be used to bring up a screen via which the customer can change any of the options for the item. Removing the item completely from the order can be done with a remove button that asks for confirmation to delete the item and, if given, then deletes the item from the order and re-displays the review order screen.

Figure 31:
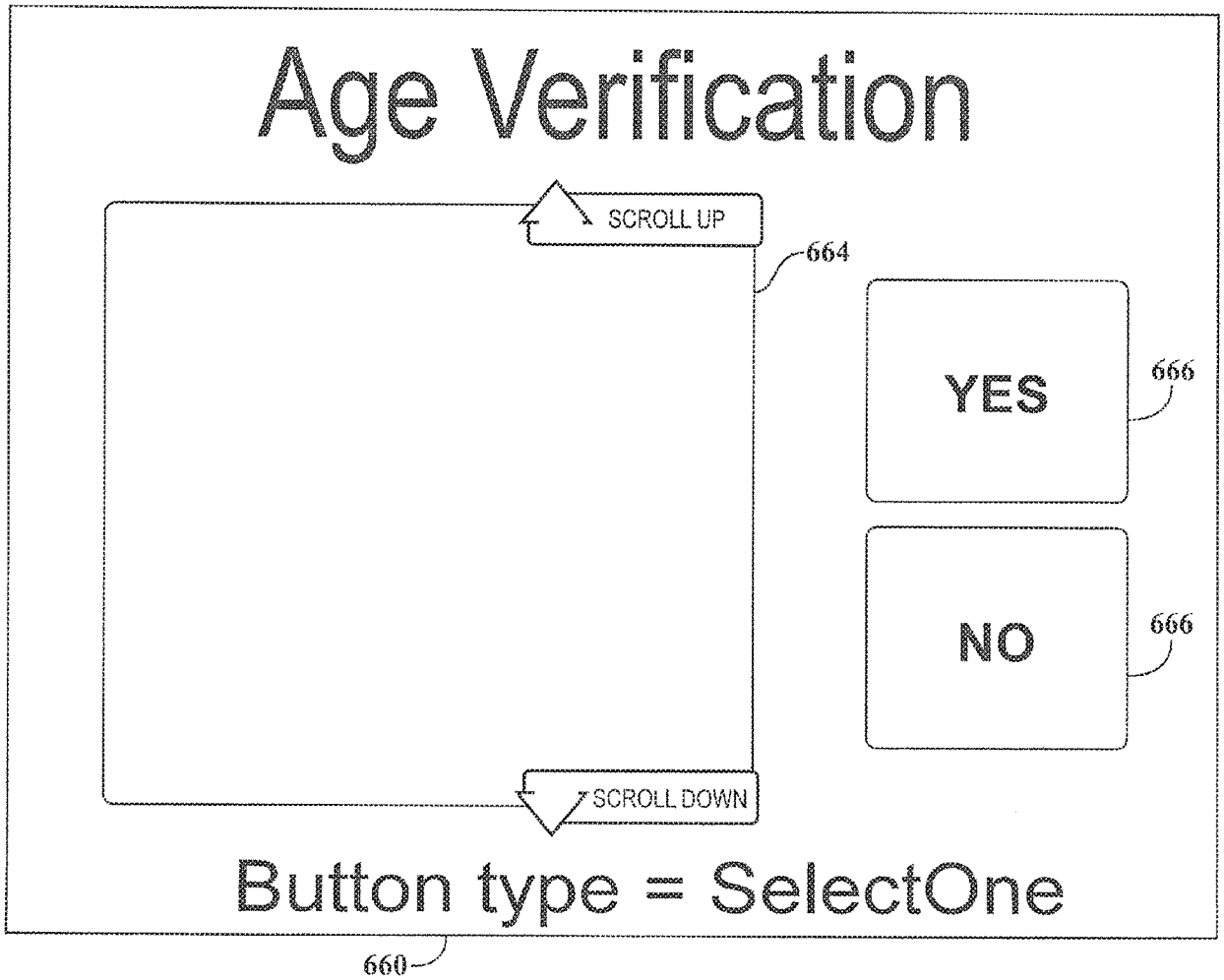
FIG. 31 illustrates an age verification template for sale of age restricted products.
Figure 32:
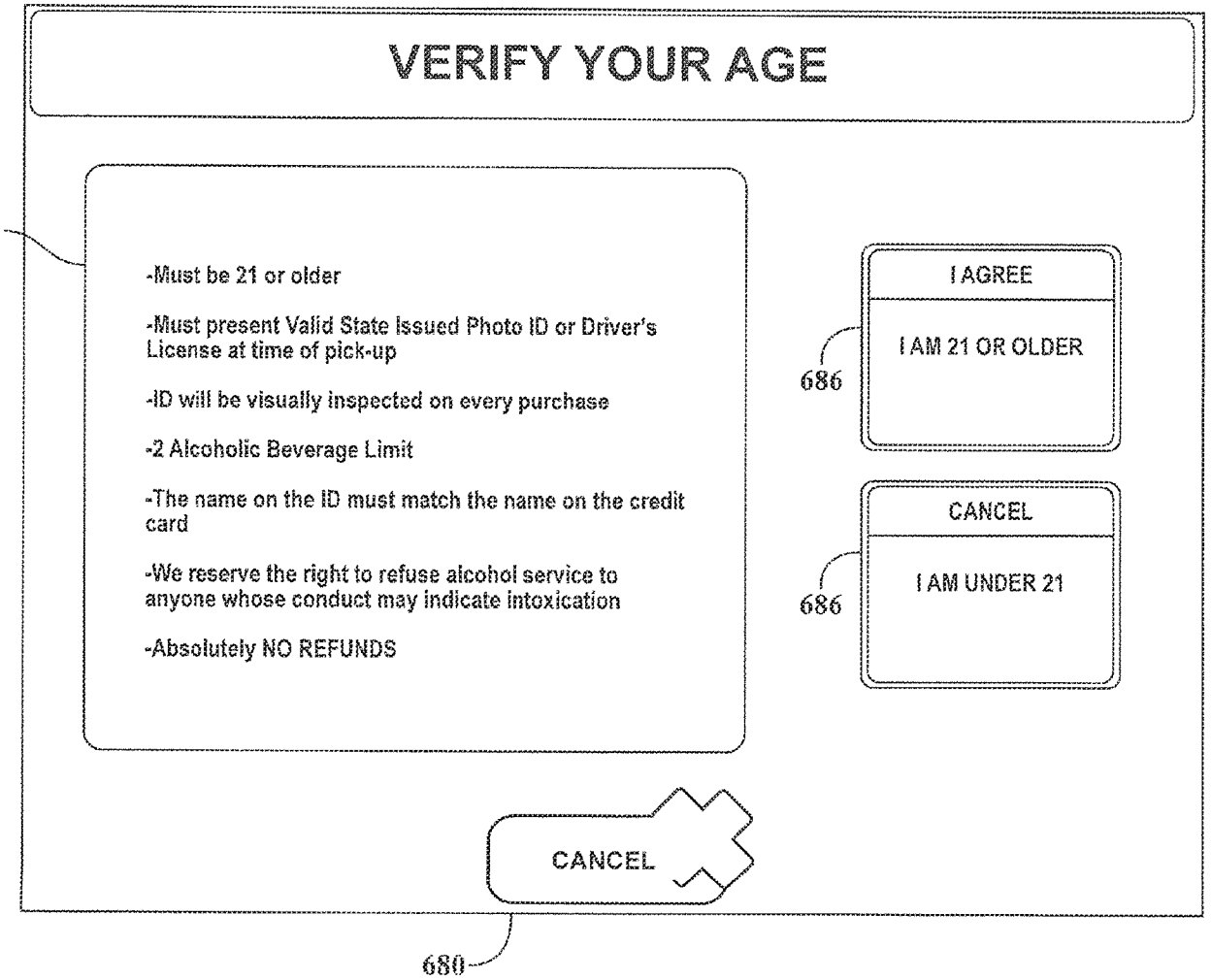
FIG. 32 illustrates the resulting screen display for the age verification template of FIG. 31.

As another example, FIGS. 31 and 32 depict an age verification template 660 (FIG. 31) and display screen 680 (FIG. 32), respectively, that require customers to verify their age for the sale of age restricted products such as alcohol. The system can be programmed to automatically use this template 660 in the event that alcohol ordering is enabled during the system setup. This template 660 contains a title, a text section 664, and a pair of MenuButtons or SelectOne buttons 666. The text section 664 enables the system to provide a detailed message to customers regarding the terms of the sale of the age-restricted product. The text section may also include a scroll bar to enable customers to view long messages that do not fit within the viewing area of the display. As shown in the resulting screen display 680, the buttons 686 require the customer to either cancel the alcohol order or acknowledge their age entitlement to purchase alcohol and to agree to the conditions 684 under which the alcohol is being sold.

Figure 33:
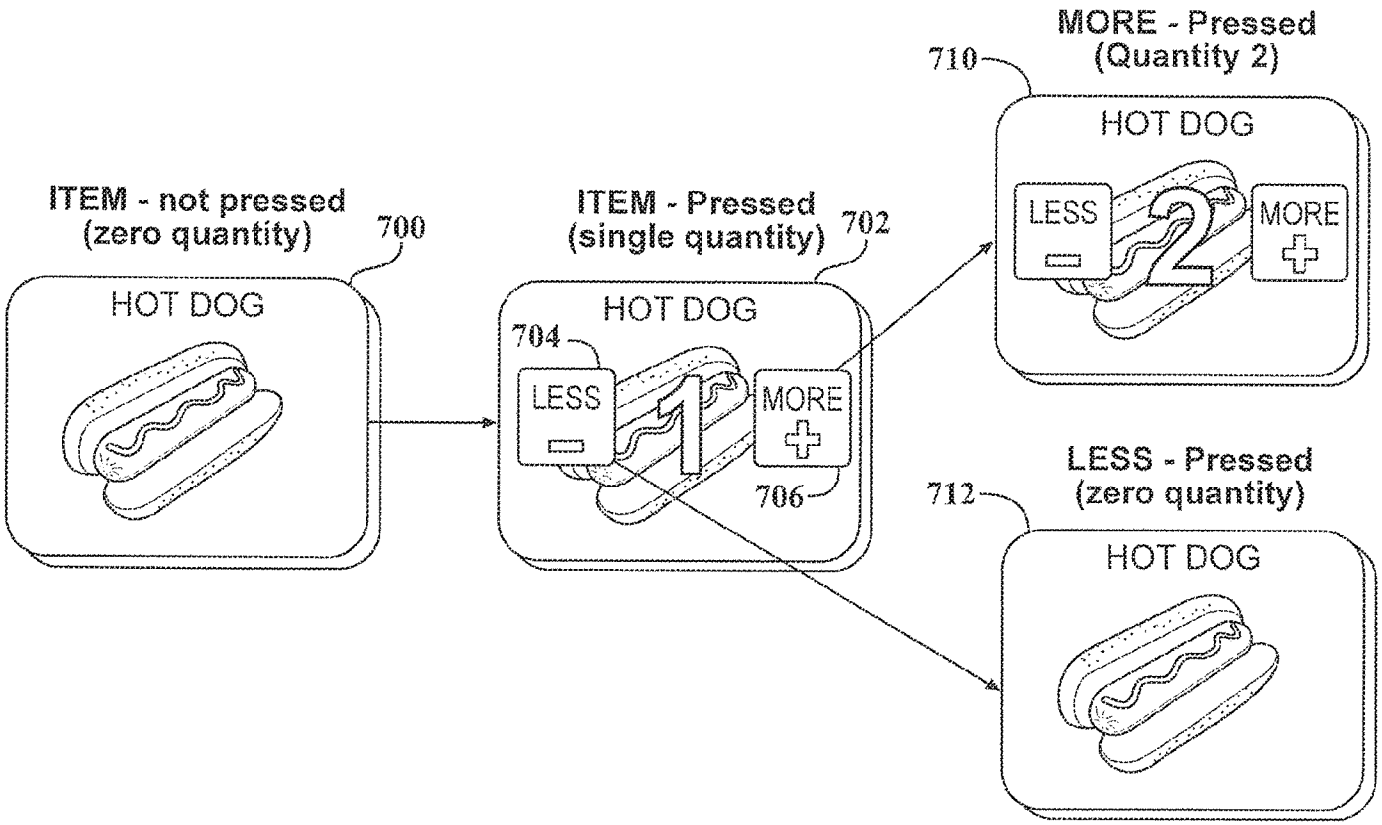
FIG. 33 illustrates an alternative quantity button including less/more overlay sub-buttons and an overlaid number count.

Apart from the Quantity button described further above that is used during ordering to bring up a keypad for number entry, and apart from the order review quantity buttons shown in FIGS. 30 and 31 that are used to change the quantity before completing the order, another type of Quantity button shown in FIG. 33 can be used as a part of the initial ordering process. This type of button is again useful for concessions ordering, but can be used in other applications as well. As shown, the button includes overlay sub-buttons that are initially hidden when the item has not been selected (button 700). Then, if the button is pressed to select the item, the center of the button has an at least partially transparent number count overlaid on the button (button 702)—initially, this count is "1" as shown. Less/More overlay buttons 704 and 706, respectively, that include a minus sign for less and a plus sign for more are provided on either side of the number count. The user can increase the quantity to be ordered by pressing the More sub-button 706 which then updates the number count, as shown at button 710. Alternatively, the user can decrease the quantity by pressing the less button 704. In the example shown in FIG. 33, pressing the less button 704 when the quantity is "1" removes the item entirely from the order, and the overlaid sub-buttons and number count are removed at button 712.

Figure 34:
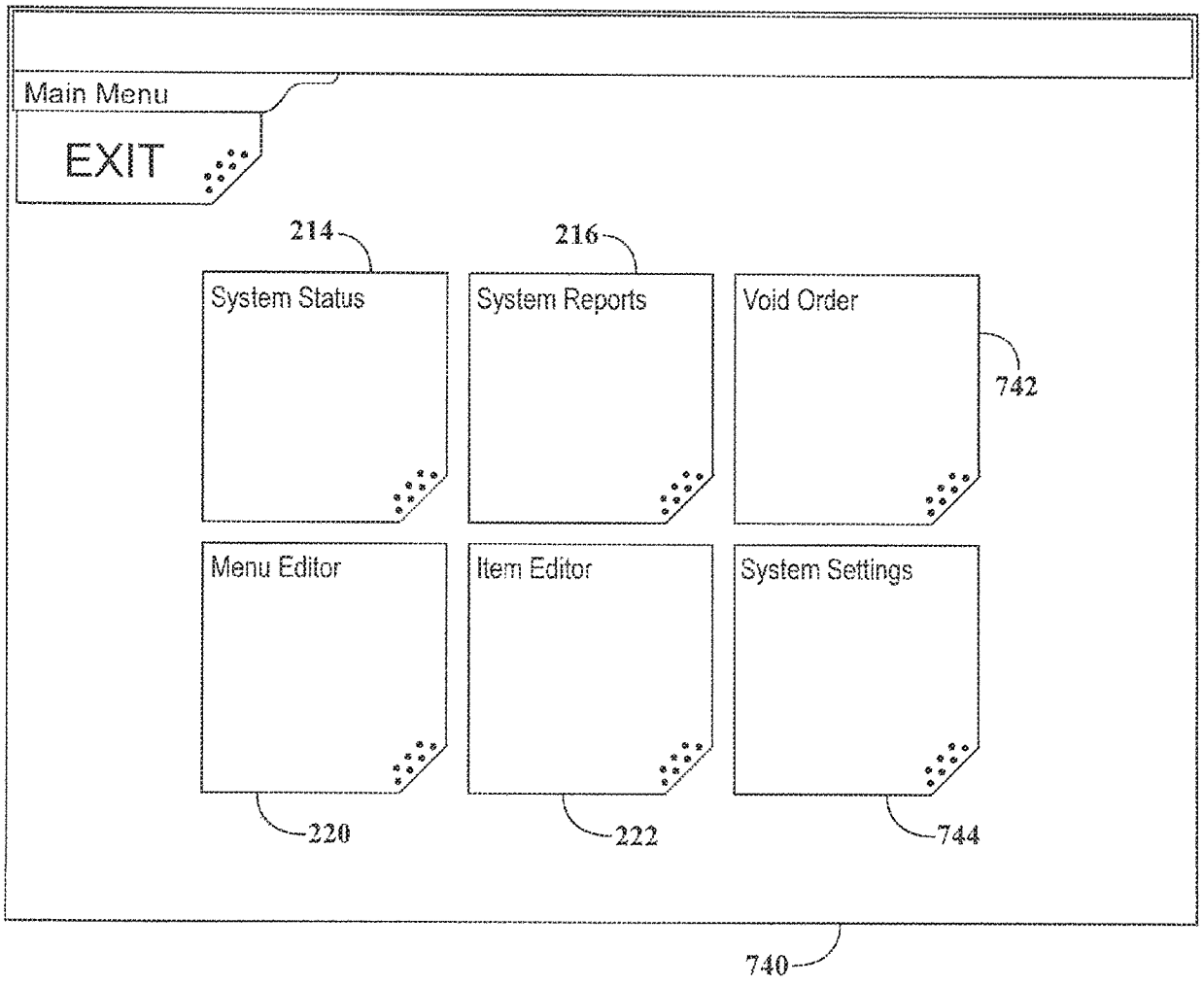
FIG. 34 illustrates an alternative administrative tool Main Menu screen, wherein the Kiosk Editor button has been replaced with a Void Order button.
Figure 35:
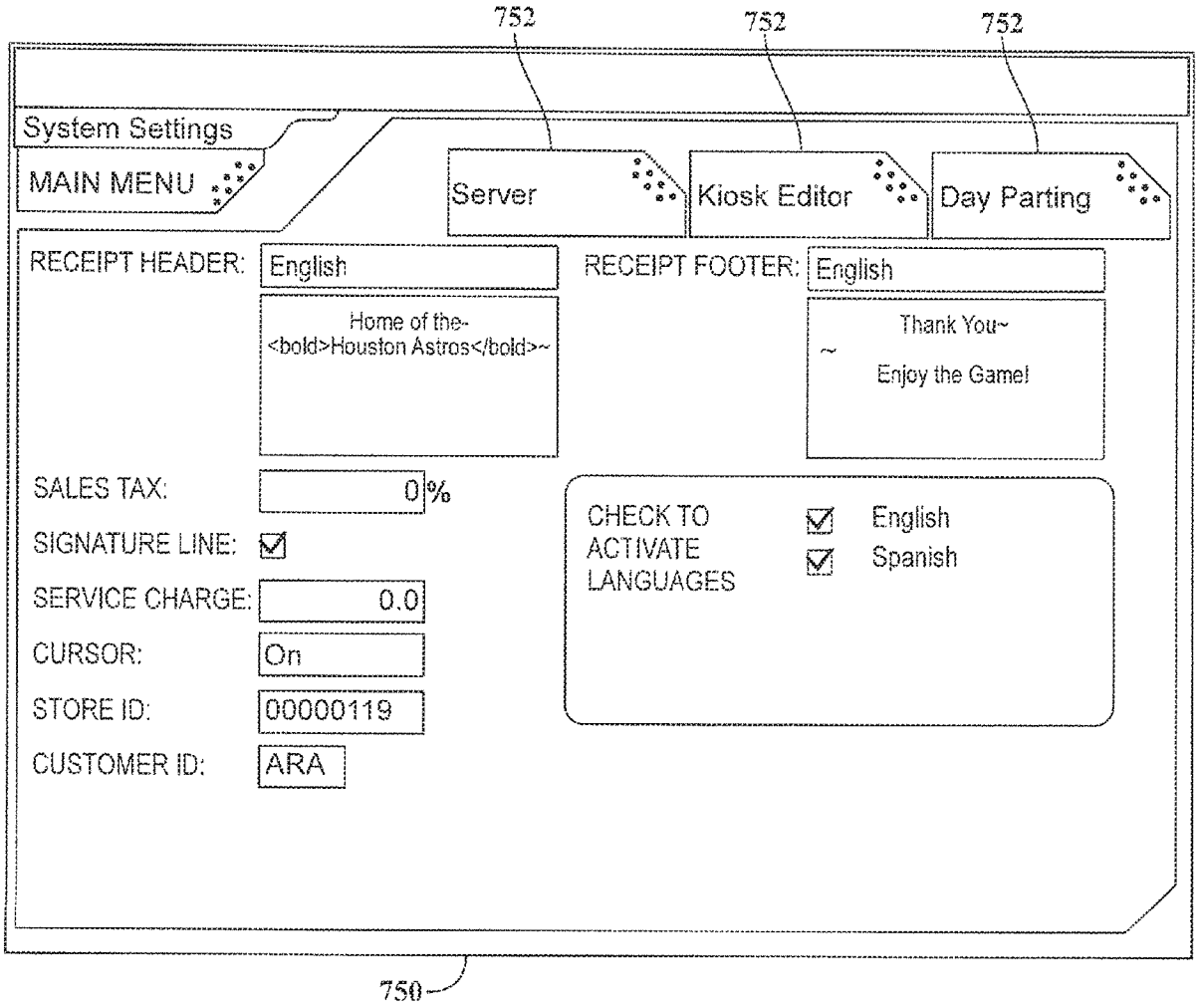
FIG. 35 illustrates a Systems Settings screen that is accessible from the Main Menu screen shown in FIG. 34.
Figure 36:
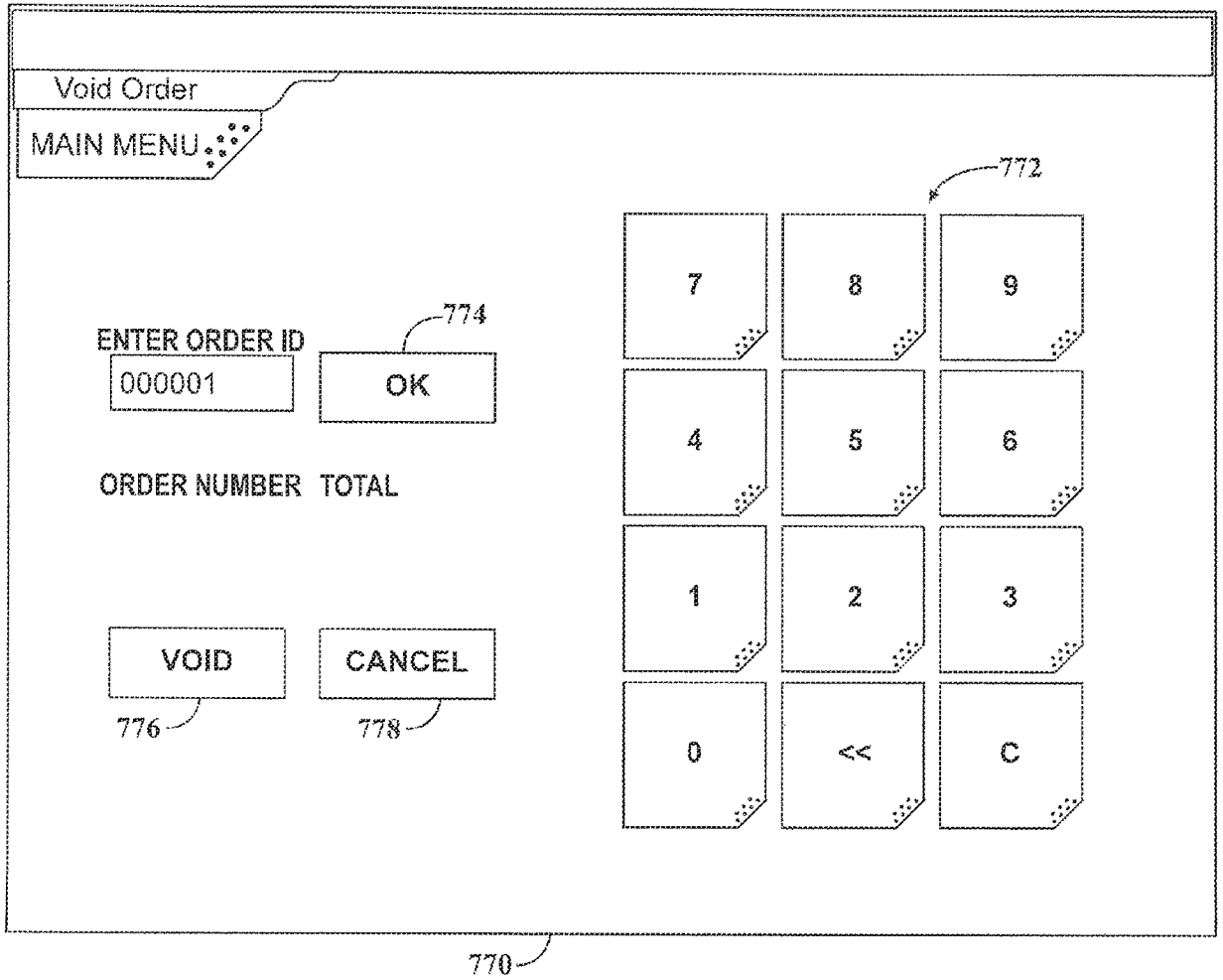
FIG. 36 illustrates a Void Order screen that is accessible from the Main Menu screen shown in FIG. 34.

In FIG. 34 there is shown an administrative tool Main Menu screen 740 that has been modified from that shown in FIG. 10. In this modified Main Menu 740, the Kiosk Editor button has been replaced with a Void Order button 742 that allows an administrator or manager to void out a customer order that has already been entered. Access to the kiosk editor functions in this embodiment are done via the Systems Settings button 744 on the Main Menu 740 which brings up the screen 750 of FIG. 35 that uses tabs 752 to provide the administrator the ability to switch between the server settings, kiosk editor, and day parting screens. FIG. 36 depicts the Void Order screen 770 that is accessed via the associated button 742 on the Main Menu 740. This screen 770 includes a keypad 772 to permit the manager or administrator to enter in an order number, press OK 774, and then have the order number and corresponding price total display, at which point the order can be voided (button 776) or left intact by pressing Cancel 778.

In a computer-based ordering system, in certain situations, it is possible that the self-service terminals could overwhelm the workers fulfilling the orders. For example, as kiosks become more prevalent in restaurants, some restaurants may put in more kiosks than the kitchen can handle and overwhelm the kitchen during peak hours. Preferred embodiments of the invention utilize an order governor to regulate the flow of orders, as needed. The preferred embodiment of the order governor is described below, with reference to FIGS. 37 and 38.

Figure 37:
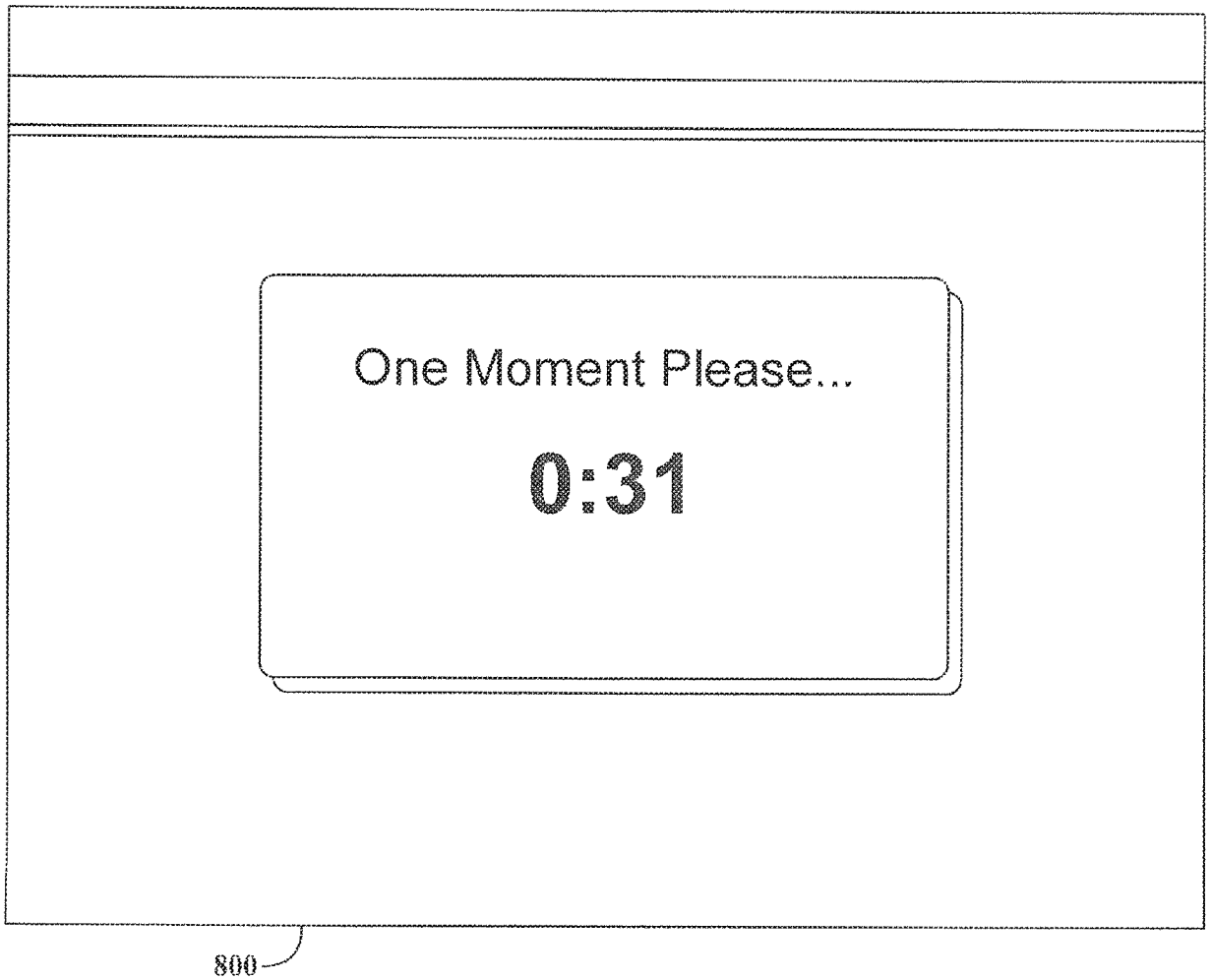
FIG. 37 illustrates a wait screen displayed by the self-order application when the order governor is enabled and the order fulfillment backlog time is greater than a predetermined value.
Figure 38:
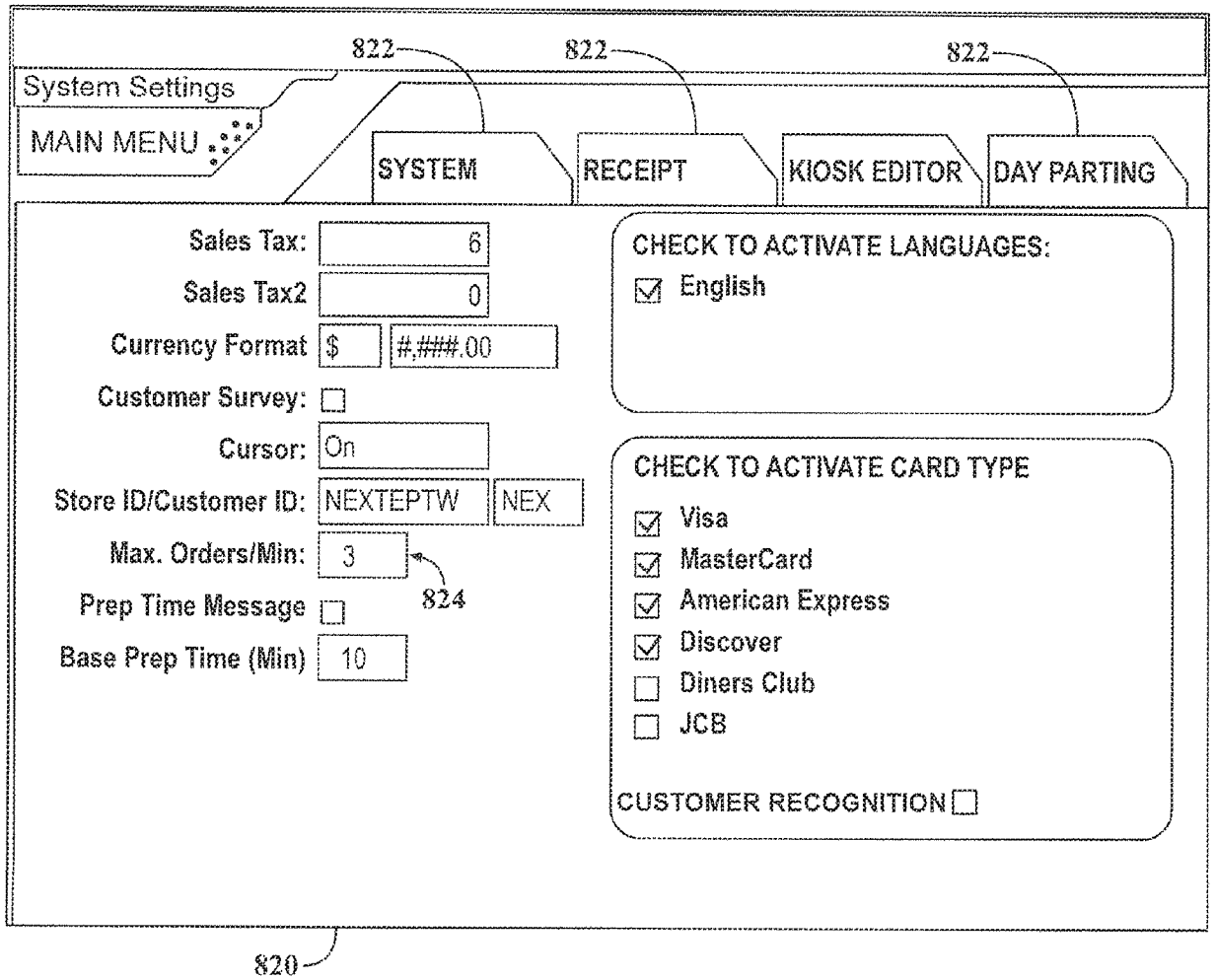
FIG. 38 illustrates a Systems Settings screen that includes a configurable value for maximum orders per minute that is used by the order governor in the exemplary order governor implementation.

With the order governor, the flow of orders is regulated by introducing a wait time between customer orders, as needed, to avoid overwhelming the workers that are fulfilling the orders. FIG. 37 depicts a wait screen 800 displayed by the self-order application when the order governor is placing the self-order application in a wait state between customer orders. The order governor configuration settings are accessible with the administration tool as shown in the System Settings screen 820 shown in FIG. 38. Screen 820 of FIG. 38 uses tabs 822 to provide the administrator the ability to switch between the system settings, receipt details, kiosk editor, and day parting screens.

In this illustrated example, the order governor includes an editable configuration value 824 for the maximum orders per minute (MOPM) that the kitchen can handle. The order governor can be disabled by setting this value to 0. Put another way, the kitchen completes an order, on average, every 60/MOPM (seconds). In the illustrated example, 3 maximum orders per minute means that an order is completed or fulfilled every 20 seconds, on average.

Each time that an order is completed at the kiosk, the kitchen backlog increases by the calculated average order fulfillment time, which in this example, is 20 seconds. That is, the order fulfillment backlog time or kitchen backlog is assigned a new value equal to the previous order fulfillment backlog time plus the configured average order fulfillment time. For example, if the current kitchen backlog for the kiosk is 10 seconds as an order is being completed at the kiosk, completion of the order increases the current kitchen backlog to 30 seconds. As time passes, for every second that passes, the kitchen backlog is decreased by one second.

In this example, when a new order is submitted, if the new total kitchen backlog is greater than one fulfillment period (20 seconds in this example), then the order governor introduces an artificial wait time at the kiosk by placing the kiosk in a wait state as shown in screen 800 of FIG. 37. If, when a new order is submitted, the new total kitchen backlog is not greater than one fulfillment period, then the wait time is not introduced, wait screen 800 of FIG. 37 is not shown, and the kiosk is immediately ready for the next order. The net effect of this described implementation is that, when there are a plurality of operating kiosks with each kiosk having an order governor, the kitchen is only allowed to get one order behind for each kiosk in operation at the store location. Of course, it is appreciated that various other implementations for the order governor are possible.

For example, the order governor configuration could include a number of configurable values representing order fulfillment time for various products. In this approach, upon completion of an order, the kitchen backlog is increased by an estimated order fulfillment time for the particular order placed. The estimation is made based on the various configured values and the particular products ordered. That is, more precise order fulfillment times are calculated instead of using a single approximation for all orders. For example, the fulfillment estimation could be based on preparation times for the items actually ordered.

In addition, it is to be appreciated that there are many possibilities for the order governor. Although the illustrated example has an order governor as part of the self-order application at each kiosk, other arrangements are possible such as a master order governor located at the server that communicates with and governs all of the client kiosks.

Figure 39:
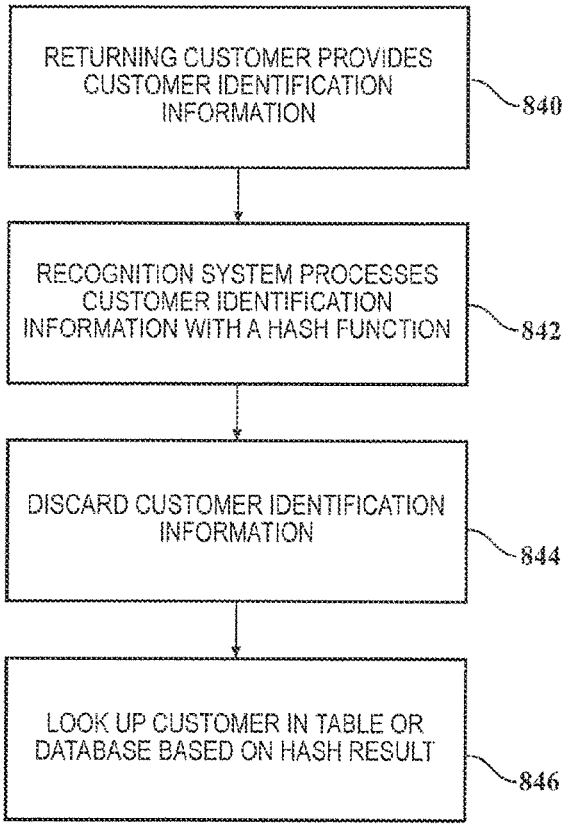
FIG. 39 illustrates an approach to customer recognition for use in computer-based ordering systems wherein, in accordance with the invention, the customer is recognized based on a hash result.

As mentioned above, the computer-based ordering system may recognize customers locally through any one of many possible methods such as, for example, swiping a customer loyalty card or bank card. Customer recognition has many advantages. One advantage of using customer recognition is that returning customers can quickly order items ordered in the past without having to rebuild the order each time they use a kiosk. In preferred embodiments of the invention, the customer is recognized without the need to permanently store sensitive information. The customer recognition system cooperates with the self-order application to recognize a returning customer when the returning customer provides customer identification information by, for example, swiping a credit card. FIG. 39 illustrates an approach to customer recognition in accordance with the invention wherein the customer is recognized based on a hash result.

As depicted at block 840, the returning customer provides customer identification information. As depicted at block 842, the recognition system processes the customer identification information with a hash function to produce a hash result. The recognition system may be implemented as part of the self-order application. It is to be appreciated that other arrangements are also possible. For example, the recognition system could be implemented at the local server or even at a remote server, depending on the implementation. Once the hash result is obtained, the customer identification information is discarded as indicated at block 844. The hash result is used to look up the customer in a table or database, as indicated at block 846. More specifically, a customer information repository, which may be located at central server 22 (FIG. 1), retains information relating to previous customer orders, preferences, or any other tracked information. The information for a particular customer is keyed by the hash result for the provided customer identification information for that customer.

Figure 40:
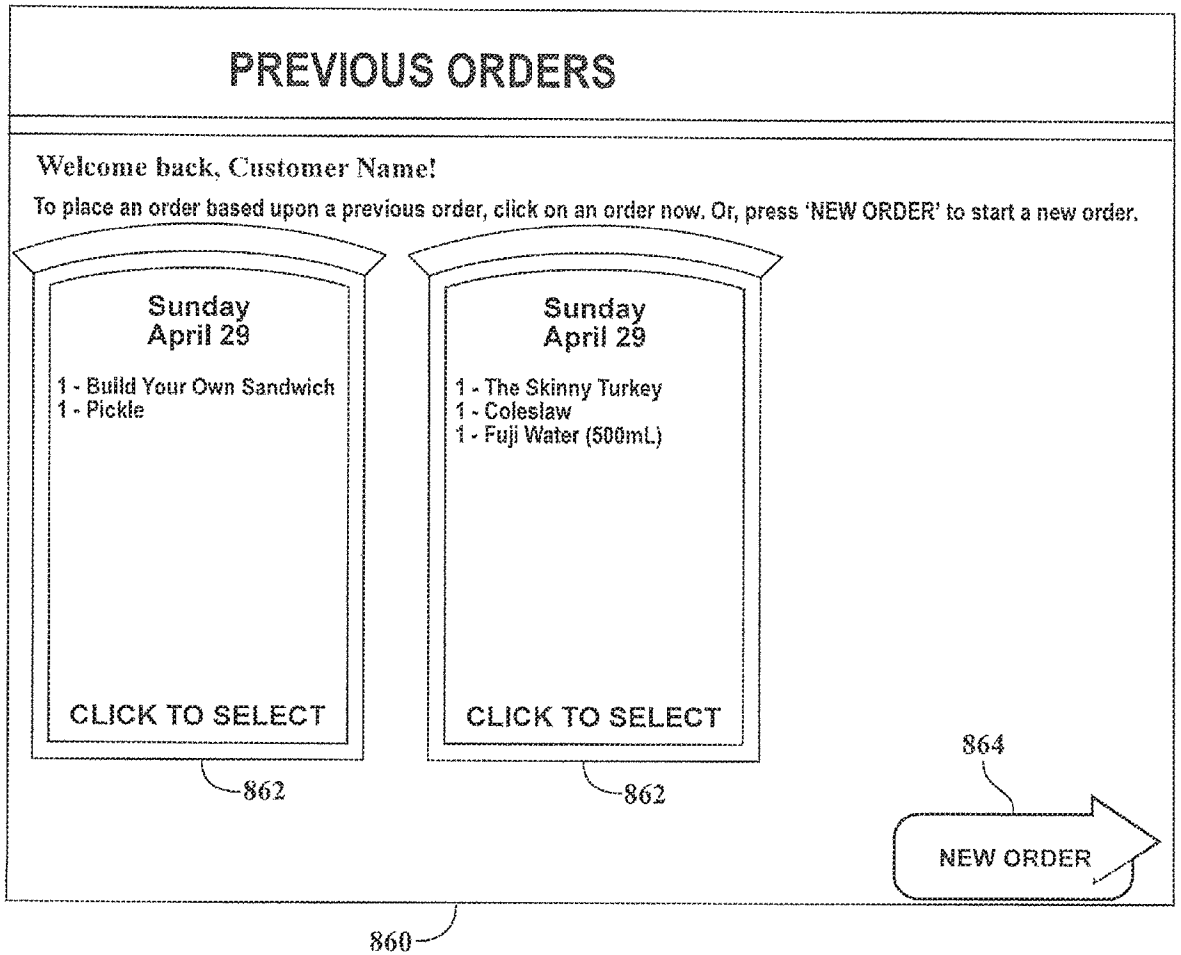
FIG. 40 illustrates a customer recognition screen displayed by the self-order application when a returning customer is recognized.

FIG. 40 illustrates a customer recognition screen 860 displayed by the self-order application when a returning customer is recognized. Previous orders 862 are displayed so that the customer, if desired, may quickly order one of the customer's previous orders without having to rebuild the order. New order button 864 allows the customer to build a new order in the case that the customer does not wish to order one of the displayed previous orders 862.

As used in this specification and appended claims, the terms "for example," "for instance," and "such as," and the verbs "comprising," "having," "including," and their other verb forms, when used in conjunction with a listing of one or more components or other items, are each to be construed as open-ended, meaning that that the listing is not to be considered as excluding other, additional components or items. Other terms are to be construed using their broadest reasonable meaning unless they are used in a context that requires a different interpretation.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

[1. A computer-based ordering system for ordering goods and services, the system comprising:

a self-service terminal for use by a customer to place an order, the self-service terminal including a processor and a storage medium storing a self-order application, the self-order application providing a first user interface including a set of interactive menu screens having buttons that allow the customer to select and customize products for the order;

the storage medium further storing an administration tool application for administering the self-service terminal, the administration tool application providing a second user interface that can be accessed by the administrator to perform various administrative functions, the administration tool application including a menu editor that enables the administrator to create and edit the interactive menu screens provided by the self-order application; and wherein the menu editor is resident in the self-service terminal accesses a library of menu templates containing predefined groupings of buttons, and uses the menu templates, as directed by the administrator, during creation and editing of the interactive menu screens.]

[2. The computer-based ordering system of claim 1 wherein the self-service terminal further comprises a display screen having a touch screen for accepting user input, and wherein the first user interface, which is provided by the self-order application, is a graphical user interface, and the customer interacts with the self-order application using the touch screen.]

[3. The computer-based ordering system of claim 1 wherein the self-service terminal further comprises a display screen having a touch screen for accepting user input, and wherein the second user interface, which is provided by the administration tool application, is a graphical user interface, and the administrator interacts with the administration tool application using the touch screen.]

[4. A computer-based ordering system for ordering goods and services, the system including a plurality of self-service client terminals for use by customers to place orders, each self-service client terminal running a self-order application, the self-order application providing a first user interface including a set of interactive menu screens having buttons that allow the customer to select and customize products for the order, the system further including a server in communication with the plurality of self-service client terminals, the system further comprising: an administration tool application stored on a computer-readable storage medium, the administration tool application being executable by a computer for communicating with the server to administer the self-service client terminals, the administration tool application providing a second user interface that can be accessed by the administrator to perform various administrative functions, the administration tool application including a menu editor that enables the administrator to create and edit the interactive menu screens provided by the self-order application at the self-service client terminals; and wherein the menu editor accesses a library of menu templates containing predefined groupings of buttons, and uses the menu templates, as directed by the administrator, during creation and editing of the interactive menu screens.]

[5. The computer-based ordering system of claim 4 wherein each self-service client terminal further comprises a display screen having a touch screen for accepting user input, and wherein the customer interacts with the self-order application using the touch screen.]

[6. The computer-based ordering system of claim 4 wherein the computer-readable storage medium storing the administration tool application is located at the server, and wherein the server further comprises a display screen having a touch screen for accepting user input, and wherein the second user interface, which is provided by the administration tool application, is a graphical user interface, and the administrator interacts with the administration tool application using the touch screen.]

[7. The computer-based ordering system of claim 4 wherein the library of menu templates includes a plurality of templates, each template representing an interactive menu screen having buttons, and wherein the menu editor enables the administrator to, during creation/editing of an interactive menu screen, select a template for the interactive menu screen and associate functions with the buttons included on the selected template.]

[8. The computer-based ordering system of claim 7 wherein associating functions with the buttons included on the selected template includes selecting a button type for a button.]

[9. The computer-based ordering system of claim 7 wherein associating functions with the buttons included on the selected template includes selecting associated text for a button.]

[10. The computer-based ordering system of claim 7 wherein associating functions with the buttons included on the selected template includes selecting an image overlay for a button.]

[11. The computer-based ordering system of claim 7 wherein associating functions with the buttons included on the selected template includes selecting an item/product for a button.]

[12. The computer-based ordering system of claim 11 wherein associating functions with the buttons included on the selected template includes selecting a quantity for the item/product for a button.]

[13. The computer-based ordering system of claim 11 wherein associating functions with the buttons included on the selected template includes selecting a pricing option for the item/product for a button.]

[14. The computer-based ordering system of claim 7 wherein associating functions with the buttons included on the selected template includes selecting a subsequent menu screen for activation upon selection of a button by the customer, thereby creating a hierarchy of menus to guide the customer through the order process.]

[15. The computer-based ordering system of claim 7 wherein the plurality of templates includes at least one template configured to allow selection of only a single button by the customer from a presented plurality of buttons.]

[16. The computer-based ordering system of claim 7 wherein the plurality of templates includes at least one template configured to allow selection of multiple buttons by a customer from a presented plurality of buttons.]

[17. The computer-based ordering system of claim 7 wherein the plurality of templates includes at least one template configured to allow selection of multiple buttons by a customer from a presented plurality of buttons, and wherein the presented plurality of buttons includes at least one special button, the special button including a plurality of sub-buttons to provide multiple selected states for the special button.]

[18. The computer-based ordering system of claim 7 wherein the plurality of templates includes at least one template configured to allow selection of multiple buttons by a customer from a presented plurality of buttons, and wherein the presented plurality of buttons includes at least one special button, the special button, upon selection thereof, causing selection of a predetermined set of the presented plurality of buttons.]

[19. A method of administrating the computer-based ordering system of claim 4, the method comprising: establishing a library of menu templates containing predefined groupings of buttons; and utilizing the menu editor of the administration tool application to create and edit the interactive menu screens for the self-order application, wherein the interactive menu screens are created using menu templates from the library.]

[20. The method of claim 19 wherein the library of menu templates includes a plurality of templates, each template representing an interactive menu screen having buttons, the method further comprising: during creation/editing of an interactive menu screen, selecting a template for the interactive menu screen and associating functions with the buttons included on the selected template.]

[21. The method of claim 19 wherein the computer-readable storage medium storing the administration tool application is located at the server.]

[22. The method of claim 21 wherein the server also operates as a self-service client terminal by running the self-order application while the server communicates with the plurality of self-service client terminals in the background.]

[23. The method of claim 21 wherein the administration tool application is also located at a plurality of the self-service client terminals to allow administration from any of the self-service client terminals having the administration tool application.]

*24. A non-transitory computer-readable medium storing instructions executable on a processor, the instructions comprising:*

*displaying menu items to a user on a display;*

*receiving input from the user via an input device;*

*in response to the input indicating selection by the user of a first menu item of the menu items, displaying a multi-part button associated with a component part of the first menu item;*

*in response to the input indicating selection by the user of any portion of the multi-part button while a plurality of additional buttons associated with the multi-part button are not visible, displaying the plurality of additional buttons, wherein each of the plurality of additional buttons corresponds respectively to a different amount of the component part in the first menu item, and wherein a first button of the plurality of additional buttons corresponds to a default for the multi-part button;*

*in response to the input indicating selection by the user of a second button of the plurality of additional buttons while another one of the plurality of additional buttons is presently selected, (i) displaying a visual indicator corresponding to the second button and (ii) maintaining visibility of the plurality of additional buttons; and*

*in response to the input indicating selection by the user of the second button while the second button is already selected, hiding the plurality of additional buttons from view of the user.*

*25. The computer-readable medium of claim 24, wherein:*

*the first menu item is a food item; and*

*the multi-part button corresponds to a first component food of the first menu item.*

*26. The computer-readable medium of claim 25, wherein the instructions further comprise, in response to the input indicating selection by the user of the first menu item, displaying a plurality of multi-part buttons including the multi-part button, wherein the plurality of multi-part buttons respectively correspond to a plurality of component foods of the first menu item.*

*27. The computer-readable medium of claim 26, wherein the plurality of component foods are condiments for the first menu item.*

*28. The computer-readable medium of claim 25, wherein one of the plurality of additional buttons corresponds to an absence of the first component food from the first menu item.*

*29. The computer-readable medium of claim 24, wherein:*

*the first button is associated with a text label of "Normal";*

*the second button is associated with a text label of "More"; and*

*a third button of the plurality of additional buttons is associated with a text label of "Less".*

*30. The computer-readable medium of claim 24, wherein the instructions further comprise selectively displaying a price differential between a price corresponding to a presently selected one of the plurality of additional buttons and a price corresponding to the first button.*

*31. The computer-readable medium of claim 24, wherein the instructions further comprise:*

*displaying an order for the user, the order including an entry listing the first menu item and displaying the total price of the first menu item; and*

*selectively updating the total price in response to changes in which of the plurality of additional buttons is selected.*

*32. The computer-readable medium of claim 24, wherein the instructions further comprise updating an order for the user based on a state of the multi-part button.*

*33. The computer-readable medium of claim 24, wherein each of the plurality of additional buttons is visually contained within a perimeter of the multi-part button.*

*34. The computer-readable medium of claim 33, wherein the plurality of additional buttons are semi-transparent.*

*35. The computer-readable medium of claim 24, wherein the visual indicator corresponding to the second button is a checkmark.*

*36. The computer-readable medium of claim 35, wherein the visual indicator corresponding to the second button is visually contained within a perimeter of the second button.*

*37. The computer-readable medium of claim 24, wherein the instructions further comprise, upon displaying the plurality of additional buttons, displaying a visual indicator corresponding to the first button.*

*38. The computer-readable medium of claim 24, wherein:*

*the multi-part button includes a text label identifying the component part; and*

*the instructions further comprise modifying the text label in response to which of the plurality of additional buttons is selected.*

*39. An apparatus comprising:*

*the computer-readable medium of claim 24;*

*the processor, wherein the processor is configured to execute the instructions from the computer-readable medium; and*

*a touchscreen that integrates the display and the input device.*

*40. A non-transitory computer-readable medium storing instructions executable on a processor, the instructions comprising:*

*displaying menu items to a user on a display;*

*receiving input from the user via an input device;*

*in response to the input indicating selection by the user of a first menu item of the menu items:*

*displaying a multi-part button associated with a component part of the first menu item;*

*displaying a plurality of additional buttons associated with the multi-part button, wherein each of the plurality of additional buttons corresponds respectively to a different amount of the component part in the first menu item, and wherein a first button of the plurality of additional buttons corresponds to a default for the multi-part button; and*

*displaying a visual indicator corresponding to the first button;*

*in response to the input indicating selection by the user of a second button of the plurality of additional buttons while another one of the plurality of additional buttons is presently selected, (i) displaying a visual indicator corresponding to the second button and (ii) maintaining visibility of the plurality of additional buttons; and*

*in response to the input indicating selection by the user of the second button while the second button is already selected, hiding the plurality of additional buttons from view of the user.*

*41. The computer-readable medium of claim 40, wherein:*

*a third button of the plurality of additional buttons corresponds to a zero amount; and*

*the instructions comprise, in response to the input indicating selection by the user of the third button, hiding the plurality of additional buttons from view of the user and omitting the component part from the first menu item in an order for the user.*

*42. The computer-readable medium of claim 41, wherein:*

*the first button is associated with a text label of "Normal";*

*the second button is associated with a text label of "Extra"; and*

*the third button is associated with a text label of "None".*

* * * * *